(12) United States Patent
Marks et al.

(10) Patent No.: US 7,569,693 B2
(45) Date of Patent: *Aug. 4, 2009

(54) NAPHTHALENE-BASED SEMICONDUCTOR MATERIALS AND METHODS OF PREPARING AND USE THEREOF

(75) Inventors: Tobin J. Marks, Evanston, IL (US); Michael R. Wasielewski, Glenview, IL (US); Antonio Facchetti, Chicago, IL (US); Brooks A. Jones, Chicago, IL (US)

(73) Assignee: Northwestern University, Evanston, IL (US)

( * ) Notice: Subject to any disclaimer, the term of this patent is extended or adjusted under 35 U.S.C. 154(b) by 50 days.

This patent is subject to a terminal disclaimer.

(21) Appl. No.: 11/811,902

(22) Filed: Jun. 12, 2007

(65) Prior Publication Data

US 2008/0021220 A1 Jan. 24, 2008

Related U.S. Application Data

(60) Provisional application No. 60/812,745, filed on Jun. 12, 2006.

(51) Int. Cl.
*C07D 471/02* (2006.01)
*H01L 21/20* (2006.01)

(52) U.S. Cl. .................. 546/66; 438/141; 438/310; 438/483; 438/796

(58) Field of Classification Search ............ 546/66; 438/310, 141, 483, 796
See application file for complete search history.

(56) References Cited

U.S. PATENT DOCUMENTS

| | | | |
|---|---|---|---|
| 2,087,133 A | 7/1937 | Vollmann | 260/124 |
| 4,378,302 A | 3/1983 | Aftergut et al. | 252/299.1 |
| 4,846,892 A | 7/1989 | Henning et al. | 106/478 |
| 5,405,962 A | 4/1995 | Muellen et al. | 546/27 |
| 5,472,494 A | 12/1995 | Hetzenegger et al. | 106/493 |
| 5,539,100 A | 7/1996 | Wasielewski et al. | |
| 5,677,417 A | 10/1997 | Muellen et al. | 528/310 |
| 5,808,073 A | 9/1998 | Böhm et al. | 546/39 |
| 5,908,583 A | 6/1999 | Havinga et al. | 252/500 |
| 5,986,099 A | 11/1999 | Müllen et al. | 546/26 |
| 6,063,181 A | 5/2000 | Bohm et al. | 106/493 |
| 6,084,099 A | 7/2000 | Hackmann et al. | 546/37 |
| 6,099,636 A | 8/2000 | Henning et al. | 106/498 |
| 6,124,458 A | 9/2000 | Müellen et al. | 546/38 |
| 6,143,905 A | 11/2000 | Bohm et al. | 549/232 |
| 6,165,661 A | 12/2000 | Hsiao et al. | |
| 6,184,378 B1 | 2/2001 | Bohm et al. | 546/37 |
| 6,252,245 B1 | 6/2001 | Katz et al. | 257/40 |
| 6,287,738 B1 | 9/2001 | Duff et al. | |
| 6,326,494 B1 | 12/2001 | Bohm et al. | 546/37 |
| 6,348,595 B1 | 2/2002 | Hendi | |
| 6,486,319 B1 | 11/2002 | Böhm et al. | 546/38 |
| 6,533,857 B1 | 3/2003 | Schmid et al. | 106/403 |
| 6,585,914 B2 | 7/2003 | Marks et al. | 252/500 |
| 6,608,323 B2 | 8/2003 | Marks et al. | 257/40 |
| 6,656,651 B1 | 12/2003 | Bender et al. | |
| 6,727,318 B1 | 4/2004 | Mathauer et al. | 524/801 |
| 6,784,301 B2 | 8/2004 | Hackmann et al. | 549/232 |
| 6,806,368 B2 | 10/2004 | Wurthner et al. | 546/37 |
| 6,878,825 B2 | 4/2005 | Krieger et al. | 546/28 |
| 6,890,377 B2 | 5/2005 | Böhm et al. | 106/31.47 |
| 6,916,928 B2 | 7/2005 | Becker et al. | 546/37 |
| 6,986,811 B2 | 1/2006 | Könemann et al. | 106/493 |
| 7,083,675 B2 | 8/2006 | Mizuguchi et al. | 106/498 |
| 7,105,046 B2 | 9/2006 | Mizuguchi et al. | 106/498 |
| 7,105,674 B2 | 9/2006 | Hackmann et al. | 546/37 |
| 7,326,956 B2 | 2/2008 | Shukla et al. | |
| 7,422,777 B2 | 9/2008 | Shukla et al. | |
| 2003/0181721 A1 | 9/2003 | Wurthner et al. | 546/37 |
| 2003/0219625 A1 | 11/2003 | Wolk et al. | 428/690 |
| 2004/0013959 A1 | 1/2004 | Bender et al. | |
| 2004/0023061 A1 | 2/2004 | Kathirgamanathan et al. | 428/690 |
| 2005/0075453 A1 | 4/2005 | Mathauer et al. | 524/801 |
| 2005/0092982 A1 | 5/2005 | Mullen et al. | 257/40 |
| 2005/0106415 A1 | 5/2005 | Jarikov et al. | 428/690 |
| 2005/0131220 A1 | 6/2005 | Dung et al. | 534/752 |
| 2005/0171252 A1 | 8/2005 | Schambony et al. | 524/90 |
| 2005/0176970 A1 | 8/2005 | Marks et al. | 549/41 |
| 2005/0222416 A1 | 10/2005 | Bohm et al. | 546/26 |
| 2005/0238974 A1 | 10/2005 | Sekiya et al. | 430/59.4 |

(Continued)

FOREIGN PATENT DOCUMENTS

DE 2951349 7/1981

(Continued)

OTHER PUBLICATIONS

Chen et al., "Tetrachloro-substituted Perylene Bisimide Dyes as Promising n-Type Organic Semiconductors: Studies on Structural, Electrochemical and Charge Transport Properties," *ChemPhysChem*, 5:137-140 (2004).

(Continued)

*Primary Examiner*—Charanjit S Aulakh
(74) *Attorney, Agent, or Firm*—K&L Gates LLP

(57) ABSTRACT

Provided are mono- and diimide naphthalene compounds for use in the fabrication of various device structures. In some embodiments, the naphthalene core of these compounds are mono-, di-, or tetra-substituted with cyano group(s) or other electron-withdrawing substituents or moieties. Such mono- and diimide naphthalene compounds also can be optionally N-substituted.

20 Claims, 10 Drawing Sheets

U.S. PATENT DOCUMENTS

| | | | |
|---|---|---|---|
| 2005/0251930 A1 | 11/2005 | Erk et al. ............... | 8/512 |
| 2006/0058330 A1 | 3/2006 | Krieger et al. .......... | 514/279 |
| 2006/0075585 A1 | 4/2006 | Krieger et al. .......... | 8/642 |
| 2006/0131564 A1 | 6/2006 | Shukla et al. ........... | 257/40 |
| 2006/0134823 A1 | 6/2006 | Shukla et al. ........... | 438/99 |
| 2006/0141287 A1 | 6/2006 | Klubek et al. ........... | 428/690 |
| 2006/0210898 A1 | 9/2006 | Jubran | |
| 2006/0229385 A1 | 10/2006 | Boehm .................... | 523/161 |
| 2006/0237712 A1 | 10/2006 | Shukla et al. | |
| 2007/0026332 A1 | 2/2007 | Ferrar et al. | |
| 2007/0096084 A1 | 5/2007 | Shukla et al. | |
| 2007/0116895 A1 | 5/2007 | Shukla et al. | |
| 2008/0135833 A1 | 6/2008 | Shukla et al. | |
| 2008/0161569 A1 | 7/2008 | Dung et al. | |
| 2008/0167435 A1 | 7/2008 | Marks et al. ............. | 526/259 |
| 2008/0177073 A1 | 7/2008 | Facchetti et al. ........ | 546/34 |
| 2008/0185555 A1 | 8/2008 | Facchetti et al. ........ | 252/182.3 |
| 2008/0185577 A1 | 8/2008 | Facchetti et al. ........ | 257/40 |
| 2008/0249309 A1 | 10/2008 | Facchetti et al. ........ | 546/37 |

FOREIGN PATENT DOCUMENTS

| | | |
|---|---|---|
| DE | 3434059 A1 | 3/1985 |
| DE | 3620332 | 12/1987 |
| DE | 3703131 | 8/1988 |
| DE | 4018830 | 12/1991 |
| DE | 4338784 | 5/1995 |
| DE | 4440242 | 5/1996 |
| DE | 19501737 | 7/1996 |
| DE | 19547210 | 6/1997 |
| DE | 19622673 | 12/1997 |
| DE | 19651712 | 6/1998 |
| DE | 19709008 A1 | 9/1998 |
| DE | 10038672 | 5/2002 |
| DE | 10148172 | 4/2003 |
| EP | 0031065 | 10/1983 |
| EP | 0 217 256 | 4/1987 |
| EP | 0 422 535 | 4/1991 |
| EP | 0 826 740 | 3/1998 |
| EP | 0 861 878 | 9/1998 |
| EP | 0 896 964 | 2/1999 |
| EP | 0 990 951 | 4/2000 |
| EP | 1 172 700 | 1/2002 |
| EP | 1 671 674 | 6/2006 |
| FR | 1 526 496 | 5/1968 |
| FR | 2 237 922 | 2/1975 |
| JP | 05-025174 | 2/1993 |
| JP | 05-027459 | 2/1993 |
| JP | 11-119455 | 4/1999 |
| JP | 2002-302674 | 10/2002 |
| JP | 2003-327587 | 11/2003 |
| JP | 2004-093801 | 3/2004 |
| JP | 2004-093802 | 3/2004 |
| JP | 2004-152815 | 5/2004 |
| JP | 2005-154409 | 6/2005 |
| JP | 2005-189765 | 7/2005 |
| JP | 2005-209887 | 8/2005 |
| JP | 2006-028027 | 2/2006 |
| WO | 90/01480 | 2/1990 |
| WO | 96/22332 | 7/1996 |
| WO | 97/22607 | 6/1997 |
| WO | 97/22608 | 6/1997 |
| WO | 97/26301 | 7/1997 |
| WO | 98/32799 | 7/1998 |
| WO | 98/32802 | 7/1998 |
| WO | 98/49164 | 11/1998 |
| WO | 00/69829 | 11/2000 |
| WO | 02/14414 | 2/2002 |
| WO | 03/091345 | 11/2003 |
| WO | 03/104232 | 12/2003 |
| WO | 2004/029028 | 4/2004 |
| WO | 2005/047265 | 5/2005 |
| WO | 2005/070894 | 8/2005 |
| WO | 2005/070895 | 8/2005 |
| WO | 2005/078023 | 8/2005 |
| WO | 2005/092901 | 10/2005 |
| WO | 2006/021307 | 3/2006 |
| WO | 2006/037539 | 4/2006 |
| WO | 2006/050860 | 5/2006 |
| WO | 2006/093965 | 9/2006 |
| WO | 2006/115714 | 11/2006 |
| WO | 2007/074137 | 7/2007 |
| WO | 2007/093643 | 8/2007 |
| WO | 2008/091670 | 7/2008 |

OTHER PUBLICATIONS

Facchetti et al., "Tuning the Semiconducting Properties of Sexithiophene by a,w-Substitution— α,ω-Diperfluorohexylsexithiophene: the First n-Type Sexithiophene for Thin-film Transistors," *Angew. Chem. Int. Ed.*, 2000: 39, 4547-4551.

Facchetti et al., "n-Type Building Blocks for Organic Electronics: a Homologous Family of Fluorocarbon-substituted Thiophene Oligomers with High Carrier Mobility," *Adv. Mater.*, 2003; 15, 33-38.

Facchetti et al., "Building Blocks for n-Type Organic Electronics. Regiochemically Modulated Inversion of Majority Carrier Sign in Perfluoroarene-Modified Polythiophene Conductors," *Angew. Chem. Int. Ed.*, 2003: 42, 3900-3903.

Jones et al., "High-Mobility Air-Stable n-Type Semiconductors with Processing Versatility: Dicyanoperylene-3,4:9,10-bis(dicarboximides)," *Angew. Chem. Int. Ed.*, 43. 6363-6366 (2004).

Jones et al., "Cyanonaphthalene Diimide Semiconductors for Air-Stable, Flexible, and Optically Transparent n-Channel Field-Effect Transistors," *American Chemical Society*, 2007: 19(11), 2703-2705.

Jones et al., "Tuning Orbital Energetics in Arylene Diimide Semiconductors. Materials Design for Ambient Stability of n-Type Charge Transport," *J. Am. Chem. Soc.*, 2007: 129, 15259-15278.

Martyushina et al., "Searches for Nondepolarizing Short-Action Myorelaxants," *Pharm. Chem.*, 1982: 16(7), 801-806 (English translation).

Müller et al., "Facile synthetic approach to novel core-extended perylene carboximide dyes," *Chem. Commun.*, (2005) 4045-4046.

Thalacker et al., "Hydrogen bond directed self-assembly of core-substituted naphthalene bisimides with melamines in solution and at the graphite interface," *Org. Biomol. Chem.*, 3:414-422 (2005).

Ahrens et al., "Cyanated Perylene-3,4-dicarboximides and Perylene-3,4:9,10-bis(dicarboximide):Facile Chromophoric Oxidants for Organic Photonics and Electronics," *Chem. Mater.*, 15:2684-2686 (2003).

Baier et al., "Intermolecular energy transfer after vibrational excitation of a perylene dye in solution, in polymer binder, and in a side-chain copolymer," *J. Chem. Phys.*, 114: 6739-6743 (2001).

Buncel et al., "Synthesis and characterization of [3,3]- and [3,4]-perinophane," *Tetrahedron Letters*, 42:3559-3562 (2001).

Database Caplus [Online] Chemical Abstracts Service, Columbus, Ohio, US; May 12, 1984, XP002493285 retrieved from STN Database accession No. 1984:34294 abstract.

Database WPI Thomason Scientific, London, GB; AN 1983-750663 XP002493286 and JP 58 124790 A (Matsushita Electric Ind. Co. Ltd.) Jul. 25, 1983, abstract.

Giaimo et al., "Excited-State Symmetry Breaking in Cofacial and Linear Dimers of a Green Perylenediimide Chlorophyll Analogue Leading to Ultrafast Charge Separation," *J. Am. Chem. Soc.*, 124: 8530-8531 (2002).

Holman et al., "Studying and Switching Electron Transfer: From the Ensemble to the Single Molecule," *J. Am. Chem. Soc.*, 126: 16126-16133 (2004).

Huttner et al., "N-type organic field effect transistors from perylene bisimide block copolymers and homopolymers," *Appl. Phys. Lett.*, 92: 093302 (2008).

Kwan et al., "Electrochemistry of Langmuir-Blodgett and Self-Assembled Films Built from Oligoimides," *Langmuir*, 8:3003-3007 (1992).

Langhals et al., "Tangentially Coupled π Systems and their Through-Space Interaction—Trichromophoric Perylene Dyes," *J. Prakt. Chem.*, 338: 654-659 (1996).

Langhals et al., "Chiral Bifluorophoric Perylene Dyes with Unusually High CD Effects—A Simple Model for the Photosynthesis Reaction Center," *Leibigs Ann./Recueil.*, 1151-1153 (1997).

Lindner et al., "Nanostructures of N-type organic semiconductor in a p-type matrix via self-assembly of block copolymers," *Macromolecules*, 37:8832-8835 (2004).

Lindner et al., "Charge Separation at Self-Assembled Nanostructured Bulk Interface in Block Copolymers," *Angew. Chem. Int. Ed.*, 45:3364-3368 (2006).

Lukas et al., "Femtosecond Optical Switching of Electron Transport Direction in Branched Donor-Acceptor Arrays," *J. Phys. Chem. B*, 104: 931-940 (2000).

Lukas et al., "Biomimetic Electron Transfer Using Low Energy Excited States: A Green Perylene-Based Analogue of Chloroophyll a," *J. Phys. Chem. B*, 106: 1299-1306 (2002).

Morris et al., "Synthesis of Extended Linear Aromatics Using Tandem Diels-Alder Aromatization Reactions,"*J. Org. Chem.*, 59:6484-6486 (1994).

Petit et al., "Synthesis of macromolecular substances comprising dye derivatives as monomeric units. III. Synthesis and study of monomeric dihydroxy dyes,"*Bulletin de la Societe Chimique de France*, 7-8:1591-1596 (1974).

Rodriguez-Llorente et al., "Infrared and Raman spectra of thin solid films of 1,2-bis(propylimido perylene) ethane," *Spectrochimica Acta. Part A*, 55: 969-978 (1999).

Rodriguez-Llorente et al., "Vibrational spectra and thin solid films of a bi(propylperylenediimide)," *J. Mater. Chem.*, 8(10): 2175-2179 (1998).

Rodriguez-Llorente et al., "Spectroscopic characterization of thin solid films of a bis(chlorobenzylimidoperyleneimido)octane derivative," *J. Mater. Chem.*, 8(3): 629-632 (1998).

Rohr et al., "Liquid crystalline coronene derivatives," *J. Mater. Chem.*, 11:1789-1799 (2001).

Shimizu et al., "Convergent Functional Groups. 15. Synthetic and Structural Studies of Large and Rigid Molecular Clefts," *J. Am. Chem. Soc.*, 116:5145-5149 (1994).

Singh et al., "Soluble derivatives of perylene and naphthalene diimide for n-channel organic field-effect transistors," *Organic Electronics*, 7:480-489 (2006).

Tauber et al., "Electron Hopping in π-Stacked Covalent and Self-Assembled Perylene Diimides Observed by ENDOR Spectroscopy," *JACS Comm.*, 128: 1782-1783 (2006).

Tsoi et al., "Distributed Bilayer Photovoltaics Based on Nematic Liquid Crystal Polymer Networks," *Chem. Mater.*, 19:5475-5484 (2007).

Annotations:
1. Replaced Figure 3 with ones in black and white,
2. Increased font size of each text, and
3. Added caption above each figure.

NAPHTHALENE-BASED SEMICONDUCTOR MATERIALS AND METHODS OF PREPARING AND USE THEREOF

CROSS REFERENCE TO RELATED APPLICATIONS

This application claims priority to and the benefit of U.S. Provisional Patent Application Ser. No. 60/812,745, filed on Jun. 12, 2006, the disclosure of which is incorporated by reference in its entirety.

STATEMENT REGARDING FEDERALLY SPONSORED RESEARCH OR DEVELOPMENT

The United States Government has certain rights to this invention pursuant to Grant Nos. N00014-02-1-0909 and N00014-05-1-0021 from the Office of Naval Research, Grant No. HR0011-05-1-0012 from the Defense Advanced Research Projects Agency (DARPA), and Grant No. DMR-0076097 from the National Science Foundation, all to Northwestern University.

BACKGROUND

The promise of large-area, flexible organic electronic devices has intrigued numerous research groups with efforts directed towards the understanding of charge injection and transport, crystal engineering of molecular solids, and device design. Various groups have been involved in the development and understanding of arylene n-type semiconductor materials for organic field-effect transistors (OFETs). As the OFET performance of molecular semiconductors has improved, the optimization of the optical and mechanical properties of these materials has advanced to yield all-organic, flexible, solution-cast, and optically transparent device structures. Particularly, transparent electronic materials in the visible region are of interest for applications in display technologies; however, current transistor technology is based upon opaque amorphous silicon. While several attempts have been made to fabricate p-channel transparent OFETs, these efforts have suffered from the large extinction coefficient absorptions in the visible spectrum for most organic semiconductors. Comparable challenges remain in the n-type context.

Among n-type organic semiconductors used in OFETs, the class of arene core diimides is one of the most investigated. The first report on a diimide-based FET was on a series of naphthalene tetracarboxylic diimides (unsubstituted core), followed by reports of perylene tetracarboxylic diimides. Over the years, chemical modification and tailoring of the imide position has resulted in the production and testing of a library of diimide-based materials. However, such compounds have been found generally to be unstable in air and have solubility characteristics that are less than satisfactory for efficient device fabrication.

SUMMARY

In light of the foregoing, it is an object of the present teachings to provide n-type semiconductor materials and/or devices and related methods for their use, thereby overcoming various deficiencies and shortcomings of the prior art, including those outlined above. It will be understood by those skilled in the art that one or more aspects of the present teachings can meet certain objectives, while one or more other aspects can meet certain other objectives. Each objective may not apply or apply equally, in all its respects, to every aspect of the present teachings. As such, the following objects can be viewed in the alternative with respect to any one aspect of the present teachings.

It is an object of the present teachings to provide one or more naphthalene mono- and/or diimide compounds core-substituted with one or more electron-withdrawing moieties, groups and/or substituents, and/or the radical anions electrochemically generated therefrom.

It is another object of the present teachings, in conjunction with the preceding, to provide such compounds with a range of available electron withdrawing N-substituted moieties, groups and/or substituents.

It is another object of the present teachings, in conjunction with the preceding, to provide such compounds with a range of available N-substituted moieties, groups and/or substituents that can improve the solubility and/or the radical anion stability of such compounds.

It is another object of the present teachings to incorporate any one or more of the present compounds into a range of device structures including, but not limited to, organic light-emitting diodes, transistors, and photovoltaic devices.

It is another object of the present teachings to use compounds of the type described herein to enhance oxidative stability and/or provide more positive reduction potential(s) of such compounds, as compared to unsubstituted polycyclic compounds of the prior art.

More specifically, the present teachings relate to naphthalene mono- and diimides that can be functionalized at various core and imide position(s) with varying moieties for improved solubility and/or radical anion stability, while maintaining strong π-π interactions and/or intermolecular coupling.

As described below, electronegative or electron-withdrawing functionalities such as, but not limited to, cyano substituents and fluorinated moieties, when substituted (e.g., N- or core substituted) on highly conjugated naphthalene structures are shown to improve electron injection. Without wishing to be bound by any particular theory, it is believed that the improved electron injection can be achieved by, without limitation, facilitating the formation of charge carriers in the form of radical anions. For example, certain embodiments of the cyano-substituted naphthalene imides of the present teachings were observed to have low reduction potentials, high solubility, and interesting optical characteristics. In particular, such core-functionalized diimide derivatives demonstrate large chemical and/or thermal stability and strong π-π intermolecular interactions. Accordingly, these compounds and others of the sort described herein can be used in the fabrication of OFETs and related device structures.

Without limitation as to any one device structure or end-use application, the present teachings can relate to compounds of a formula selected from

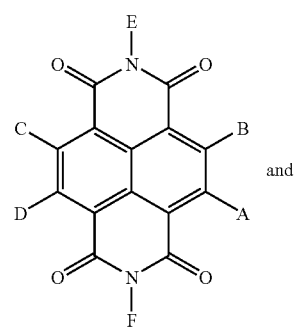

and

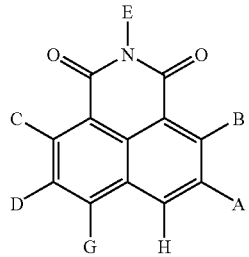

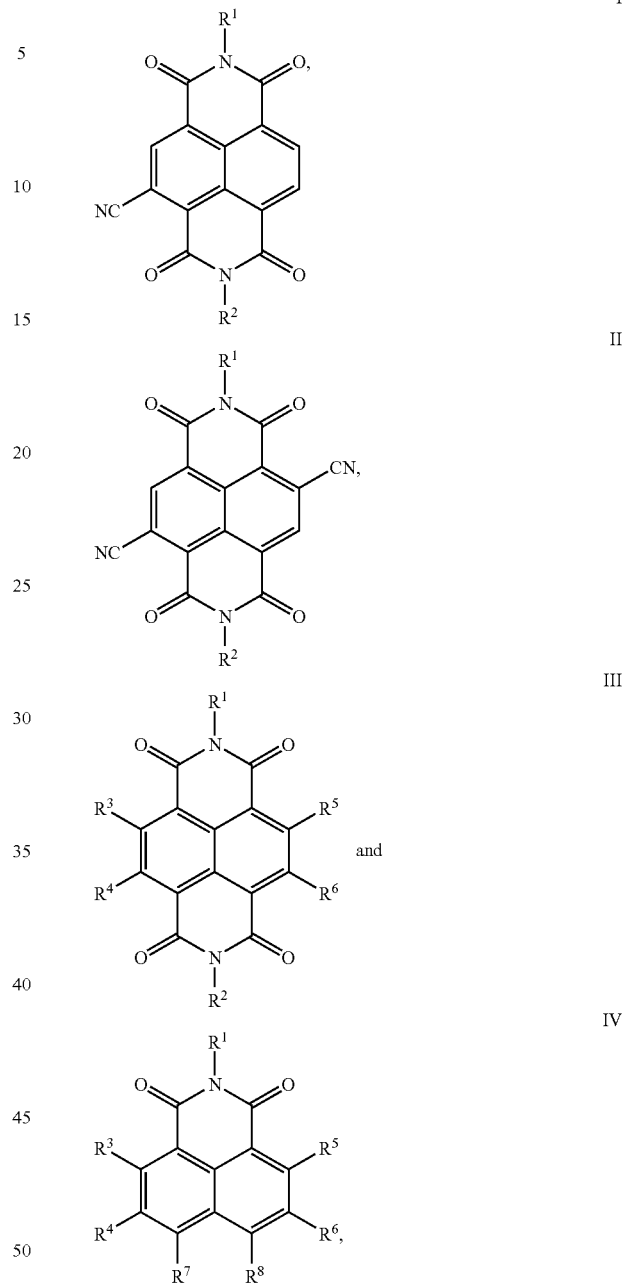

wherein each of A-D and G-H can be independently selected from H, an electron-withdrawing substituent and a moiety comprising such a substituent. Electron-withdrawing substituents include, but are not limited to, nitro, cyano, quarternary amino, sulfo, carbonyl, substituted carbonyl and carboxy substituents. Associated moieties can be, but are not limited to, alkyl, substituted alkyl, cycloalkyl, substituted cycloalkyl, aryl, substituted aryl, polycyclic aryl and substituted polycyclic aryl moieties. Without limitation, such moieties and associated electron-withdrawing substituents can be selected from $C_nF_{2n+1}$, $C_nH_2F_{2n-1}$ and C(O)R (e.g., R=H, alkyl, $C_nF_{2n+1}$ or $C_nH_2F_{2-1}$) groups—as would be understood by those skilled in the art and made aware of the present teachings. The present compounds generally include at least one of A-D and G-H selected from one of such substituents and/or associated moieties. In some embodiments, E and F are independently selected from H, alkyl, substituted alkyl, cycloalkyl, substituted cycloalkyl, aryl, substituted aryl, polycyclic aryl and substituted polycyclic aryl moieties. Any such moiety can comprise one or more of the aforementioned electron-withdrawing substituents. For example, without limitation, certain substituted alkyl moieties can include $C_nH_{2+1}$, $C_nF_{2n+1}$, $C_nH_2F_{2n-1}$ and the like. Further, one or more methylene (—CH$_2$—) or methene (—CH=) components of any such alkyl or aryl moiety can be substituted with a heteroatom (e.g., O or N) to provide the corresponding substituted moiety (e.g., ether, amine, polyether, polyamine and corresponding heteroaromatic moieties).

In some embodiments, at least one of A-D, G and H can be either an electron-withdrawing substituent or a moiety comprising such a substituent. In certain embodiments, such electron-withdrawing substituents can be selected from fluorine and various substituents having a Hammett $\sigma^+$ value greater than or equal to 0.3. Without limitation, at least one of A-D, G and H can be a cyano substituent. In certain embodiments, as discussed more fully below, such cyanated compounds can be mono-, di- or tetra-substituted. Regardless of core substitution, in certain embodiments, at least one of E and F can be optionally substituted regardless of any particular pattern or degree of core substitution.

Particular embodiments of the present teachings relate to compounds having a formula selected from:

wherein $R^1$, $R^2$, $R^3$, $R^4$, $R^5$, $R^6$, $R^7$ and $R^8$ are as defined hereinbelow.

Without regard to any particular end-use application, the present teachings can be directed to composites of the type incorporated into a range of device structures. Such a composite can comprise a suitable substrate and a semiconductor component, with or without the presence of any additional functional layer, film or component therebetween. Such a semiconductor component can comprise one or more compounds of a formula selected from the core-substituted and optionally N-substituted compounds as described herein. In certain embodiments, such a composite can be incorporated into a transistor (e.g., an OFET) or another device structure. Regardless, core substitution can be used to enhance oxidative stability and/or to lower the reduction potential(s) of such a compound, as compared to unsubstituted naphthalene compounds of the prior art, to increase solubility and/or to improve device performance.

The foregoing, other features, and advantages of the present teachings, will be more fully understood from the following figures, description, and claims.

BRIEF DESCRIPTION OF DRAWINGS

It should be understood that certain drawings are not necessarily to scale, with emphasis generally being placed upon illustrating the principles of the present teachings. The drawings are not intended to limit the scope of the present teachings in any way.

FIG. 1a depicts the face-on-view, while FIG. 1b shows the side view which depicts a nearly planar naphthalene core. FIG. 1c shows the packing diagram demonstrating a small intermolecular distance of ~3.1 Å (N,N'-groups have been removed for clarity).

FIG. 9b: transfer plot) and an NDI-8CN$_2$ device (FIG. 9c: output plots at −40 V, −20 V, 0 V, 20 V, 40 V, 60 V, 80 V, and 100V; FIG. 9d: transfer plot) according to the present teachings.

FIG. 10b: transfer plot) and an NDI-8CN$_2$ OFET device (FIG. 10c: output plots at −40 V, −20 V, 0 V, 20 V, 40 V, 60 V, 80 V, and 100V; FIG. 10d: transfer plot) according to the present teachings.

FIGS. 14a-b are output plots showing the transistor characteristics for a device fabricated on an overhead transparency film with a PEDOT:PSS (1:1) gate and a polymeric dielectric (inset) (FIG. 14a) and a device fabricated on an ITO/glass substrate with a polymer dielectric (inset) (FIG. 14b). FIGS. 14c-d are the corresponding transfer plots for the two devices. FIG. 14c is the transfer plot of the PEDOT:PSS-gated device which exhibited μ=0.03 cm$^2$V$^{-1}$s$^{-1}$, V$_{th}$=−2 V, I$_{on}$/I$_{off}$=10$^3$. FIG. 14c (inset) further shows an optical micrograph of a device array with the NDI-8CN$_2$ structure in the background demonstrating device transparency. FIG. 14d is the transfer plot of the ITO-gated device which exhibited μ=0.08 cm$^2$V$^{-1}$s$^{-1}$, V$_{th}$=4 V, I$_{on}$/I$_{off}$=10$^3$. FIG. 14d (inset) shows an optical micrograph of a device array with the NDI-8CN$_2$ structure in the background demonstrating device transparency.

DETAILED SPECIFICATION

Figure 1:
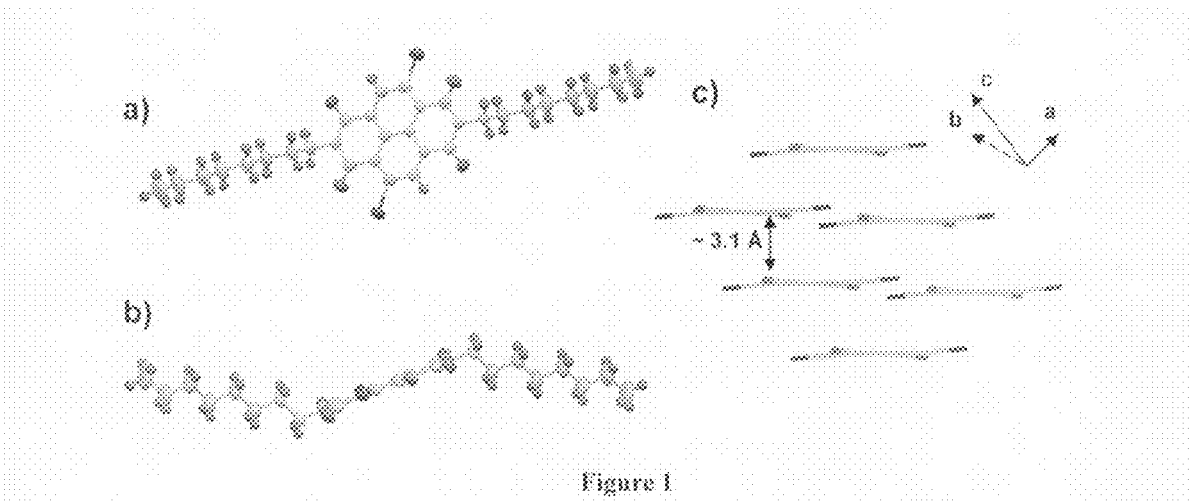
FIGS. 1a-c show the crystal structure of a compound according to the present teachings, in particular, NDI-8Br$_2$.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions may be conducted simultaneously.

As used herein, "halo" or "halogen" refers to fluoro, chloro, bromo, and iodo.

As used herein, "alkyl" refers to a straight-chain or branched saturated hydrocarbon group. In some embodiments, an alkyl group can have from 1 to 20 carbon atoms (e.g., from 1 to 6 carbon atoms). Examples of alkyl groups include methyl (Me), ethyl (Et), propyl (e.g., n-propyl and isopropyl), butyl (e.g., n-butyl, isobutyl, s-butyl, t-butyl), pentyl groups (e.g., n-pentyl, isopentyl, neopentyl), and the like. In some embodiments, alkyl groups can be substituted as described herein. A lower alkyl group typically has up to 6 carbon atoms, i.e., one to six carbon atoms. Examples of lower alkyl groups include methyl, ethyl, propyl (e.g., n-propyl and isopropyl), and butyl groups (e.g., n-butyl, isobutyl, s-butyl, t-butyl).

As used herein, "alkenyl" refers to a straight-chain or branched alkyl group having one or more carbon-carbon double bonds. In some embodiments, an alkenyl group can have from 2 to 20 carbon atoms (e.g., from 2 to 6 carbon atoms). Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In some embodiments, alkenyl groups can be substituted as described herein.

As used herein, "alkynyl" refers to a straight-chain or branched alkyl group having one or more carbon-carbon triple bonds. In some embodiments, an alkynyl group can have from 2 to 20 carbon atoms (e.g., from 2 to 6 carbon atoms). Examples of alkynyl groups include ethynyl, propynyl, butynyl, pentynyl, and the like. The one or more carbon-carbon triple bonds can be internal (such as in 2-butyne) or terminal (such as in 1-butyne). In some embodiments, alkynyl groups can be substituted as described herein.

As used herein, "haloalkyl" refers to an alkyl group having one or more halogen substituents. In some embodiments, a haloalkyl group can have from 1 to 20 carbon atoms (e.g., from 1 to 6 carbon atoms). Examples of haloalkyl groups include $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups wherein all of the hydrogen atoms are replaced with halogen atoms (e.g., $CF_3$ and $C_2F_5$), are included within the definition of "haloalkyl."

As used herein, "cycloalkyl" refers to a non-aromatic carbocyclic group including cyclized alkyl, alkenyl, and alkynyl groups. A cycloalkyl group can be monocyclic (e.g., cyclohexyl) or polycyclic (e.g., containing fused, bridged, and/or spiro ring systems), wherein the carbon atoms are located inside or outside of the ring system. A cycloalkyl group, as a whole, can have from 3 to 14 ring atoms (e.g., from 3 to 8 carbon atoms for a monocyclic cycloalkyl group and from 7 to 14 carbon atoms for a polycyclic cycloalkyl group). Any suitable ring position of the cycloalkyl group can be covalently linked to the defined chemical structure. Examples of cycloalkyl groups include cyclopropyl, cyclopropylmethyl, cyclobutyl, cyclopentyl, cyclohexyl, cyclohexylmethyl, cyclohexylethyl, cycloheptyl, cyclopentenyl, cyclohexenyl, cyclohexadienyl, cycloheptatrienyl, norbornyl, norpinyl, norcaryl, adamantyl, and spiro[4.5]decanyl groups, as well as their homologs, isomers, and the like. In some embodiments, cycloalkyl groups can be substituted with as described herein.

As used herein, "heteroatom" refers to an atom of any element other than carbon or hydrogen and includes, for example, nitrogen, oxygen, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have from 6 to 14 carbon atoms in its ring system, which can include multiple fused rings. In some embodiments, a polycyclic aryl group can have from 8 to 14 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic) and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be optionally substituted as described herein.

As used herein, "cycloheteroalkyl" refers to a non-aromatic cycloalkyl group that contains at least one ring heteroatom selected from O, N and S, which may be the same or different, and optionally contains one or more double or triple bonds. A cycloheteroalkyl group, as a whole, can have, for example, from 3 to 14 ring atoms and contains from 1 to 5 ring heteroatoms (e.g., from 3-7 ring atoms for a monocyclic cycloheteroalkyl group and from 7 to 14 ring atoms for a polycyclic cycloheteroalkyl group). In some embodiments, nitrogen atoms of cycloheteroalkyl groups can bear a substituent as described herein. Examples of cycloheteroalkyl groups include, among others, morpholine, thiomorpholine, pyran, imidazolidine, imidazoline, oxazolidine, pyrazolidine, pyrazoline, pyrrolidine, pyrroline, tetrahydrofuran, tetrahydrothiophene, piperidine, piperazine, and the like. In some embodiments, cycloheteroalkyl groups can be optionally substituted as described herein.

As used herein, "heteroaryl" refers to an aromatic monocyclic ring system containing at least 1 ring heteroatom selected from oxygen (O), nitrogen (N) and sulfur (S) or a polycyclic ring system where at least one of the rings present in the ring system is aromatic and contains at least 1 ring heteroatom. When more than one ring heteroatoms are present they may be the same or different. Polycyclic heteroaryl groups include two or more heteroaryl rings fused together and monocyclic heteroaryl rings fused to one or more aromatic carbocyclic rings, non-aromatic carbocyclic rings, and/or non-aromatic cycloheteroalkyl rings. A heteroaryl group, as a whole, can have, for example, from 5 to 14 ring atoms and contain 1-5 ring heteroatoms. The heteroaryl group can be attached to the defined chemical structure at any heteroatom or carbon atom that results in a stable structure.

Generally, heteroaryl rings do not contain O—O, S—S, or S—O bonds. Examples of heteroaryl groups include, for example, the 5-membered monocyclic and 5-6 bicyclic ring systems shown below:

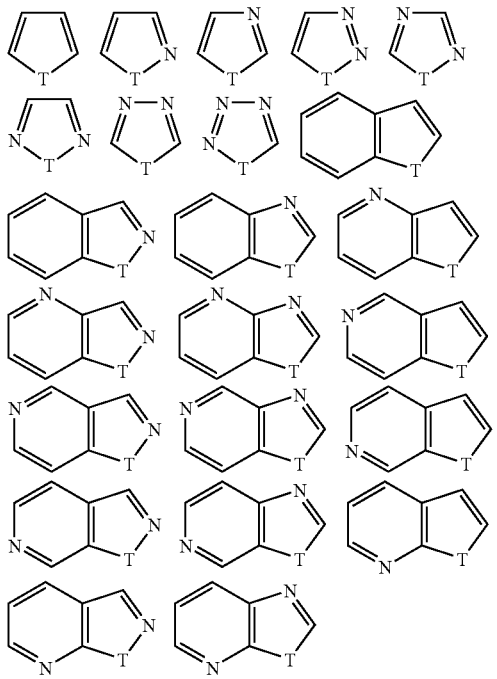

wherein T is O, S, NH, and NR$^a$; and R$^a$ is as described herein. Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

The compounds of the present teachings can include a "divalent group" defined herein as a linking group capable of forming a covalent bond with two other moieties. For example, compounds described herein can include a divalent $C_{1-10}$ alkyl group, such as, for example, a methylene group, and for example, as part of a —($C_{1-20}$ alkyl)-$C_{6-14}$ aryl group.

At various places in the present specification, substituents of compounds are disclosed in groups or in ranges. It is specifically intended that the description include each and every individual subcombination of the members of such groups and ranges. For example, the term "$C_{10}$ alkyl" is specifically intended to individually disclose $C_1$, $C_2$, $C_3$, $C_4$, $C_5$, $C_6$, $C_7$, $C_8$, $C_9$, $C_{10}$, $C_1$-$C_{10}$, $C_1$-$C_9$, $C_1$-$C_8$, $C_1$-$C_7$, $C_1$-$C_6$, $C_1$-$C_5$, $C_1$-$C_4$, $C_1$-$C_3$, $C_1$-$C_2$, $C_2$-$C_{10}$, $C_2$-$C_9$, $C_2$-$C_8$, $C_2$-$C_7$, $C_2$-$C_6$, $C_2$-$C_5$, $C_2$-$C_4$, $C_2$-$C_3$, $C_3$-$C_{10}$, $C_3$-$C_9$, $C_3$-$C_8$, $C_3$-$C_7$, $C_3$-$C_6$, $C_3$-$C_5$, $C_3$-$C_4$, $C_4$-$C_{10}$, $C_4$-$C_9$, $C_4$-$C_8$, $C_4$-$C_7$, $C_4$-$C_6$, $C_4$-$C_5$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$, and $C_9$-$C_{10}$ alkyl. By way of other examples, the term "5-14 membered heteroaryl group" is specifically intended to individually disclose a heteroaryl group having 5, 6, 7, 8, 9, 10, 11, 12, 13, 14, 5-14, 5-13, 5-12, 5-11, 5-10, 5-9, 5-8, 5-7, 5-6, 6-14, 6-13, 6-12, 6-11, 6-10, 6-9, 6-8, 6-7, 7-14, 7-13, 7-12, 7-11, 7-10, 7-9, 7-8, 8-14, 8-13, 8-12, 8-11, 8-10, 8-9, 9-14, 9-13, 9-12, 9-11, 9-10, 10-14, 10-13, 10-12, 10-11, 11-14, 11-13, 11-12, 12-14, 12-13, and 13-14 ring atoms; and the phrase "optionally substituted with 1-5 substituents" is specifically intended to individually disclose a chemical group that can include 0, 1, 2, 3, 4, 5, 0-5, 0-4, 0-3, 0-2, 0-1, 1-5, 1-4, 1-3, 1-2, 2-5, 2-4, 2-3, 3-5, 3-4 and 4-5 substituents.

Throughout the specification, structures may or may not be presented with chemical names. Where any question arises as to nomenclature, the structure prevails.

The present teachings relate to naphthalene mono- and diimides that can be functionalized at various core and imide position(s) with varying moieties for improved solubility and/or radical anion stability, while maintaining strong π-π interactions and/or intermolecular coupling. The choice of moiety or functional group can vary as described herein but can take into consideration at least the following four factors: 1) the electron-withdrawing capability; 2) the capability of attachment to the π-conjugated core; 3) the potential for increased solubility of the compound for solution processing, and/or 4) the strong π-π interactions and/or intermolecular coupling. To illustrate, FIGS. 1a-c show the crystal structure of a compound according to the present teachings, in particular, NDI-8Br$_2$. FIG. 1a depicts the face-on-view, while FIG. 1b shows the side view which depicts a nearly planar naphthalene core. FIG. 1c shows the packing diagram demonstrating a small intermolecular distance of ~3.1 Å (N,N'-groups have been removed for clarity). The present compounds and related methods can be employed to enhance the performance of the associated devices (e.g., OFETs).

More specifically, an aspect of the present teachings relates to optionally N-substituted 2-cyanonaphthalene-1,4,5,8-bis(dicarboximide)s, optionally N-substituted 2,3-dicyanonaphthalene-1,4,5,8-bis(dicarboximide)s, optionally N-substituted 2,6-dicyanonaphthalene-1,4,5,8-bis(dicarboximide)s, and optionally N-substituted 2,3,6,7-tetracyanonaphthalene-1,4,5,8-bis(dicarboximide)s. Certain embodiments of these compounds can have a formula selected from:

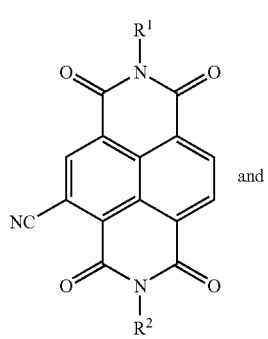

and

I

-continued

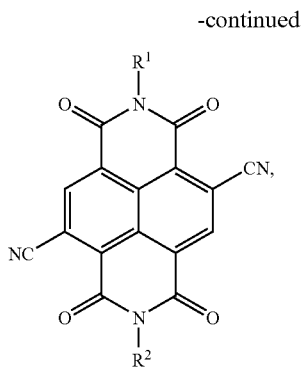

II wherein:

R¹ and R² independently are selected from a) H, b) a $C_{1-20}$ alkyl group, c) a $C_{1-20}$ haloalkyl group, d) a $C_{2-20}$ alkenyl group, e) a $C_{2-20}$ alkynyl group, f) a $C_{3-14}$ cycloalkyl group, g) a $C_{6-14}$ aryl group, h) a 3-14 membered cycloheteroalkyl group, and i) a 5-14 membered heteroaryl group, wherein each of the $C_{1-20}$ alkyl group, the $C_{2-20}$ alkenyl group, the $C_{2-20}$ alkynyl group, the $C_{3-14}$ cycloalkyl group, the $C_{6-14}$ aryl group, the 3-14 membered cycloheteroalkyl group, and the 5-14 membered heteroaryl group is optionally substituted with 1-5 $R^a$ groups;

$R^a$, at each occurrence, is independently selected from a) a halogen, b) —CN, c) —NO₂, d) —N⁺(R^b)₃, e) —S(O)_mR^b, f) —S(O)_mOR^b, g) —C(O)R^b, h) —C(O)OR^b, i) —(CH₂CH₂O)_nCH₂CH₂OH, and j) a $C_{1-20}$ haloalkyl group;

$R^b$, at each occurrence, is independently selected from a) H, b) a $C_{1-20}$ alkyl group, c) a $C_{1-20}$ haloalkyl group, d) a $C_{6-14}$ aryl group, e) a —($C_{1-20}$ alkyl)-$C_{6-14}$ aryl group, and f) a —$C_{1-20}$ haloalkyl)-$C_{6-14}$ aryl group;

m is 0, 1 or 2; and n is 1, 2, 3, 4, 5, 6, 7, 8, 9 or 10.

In some embodiments of compounds of formula I or II, R¹ and R² independently can be selected from a $C_{1-20}$ alkyl group, a $C_{1-20}$ haloalkyl group, a $C_{2-20}$ alkenyl group, a $C_{2-20}$ alkynyl group, a $C_{3-14}$ cycloalkyl group, a $C_{6-14}$ aryl group, a 3-14 membered cycloheteroalkyl group, and a 5-14 membered heteroaryl group, wherein each of the $C_{1-20}$ alkyl group, the $C_{2-20}$ alkenyl group, the $C_{2-20}$ alkynyl group, the $C_{3-14}$ cycloalkyl group, the $C_{6-14}$ aryl group, the 3-14 membered cycloheteroalkyl group, and the 5-14 membered heteroaryl group can be optionally substituted with 1-5 $R^a$ groups, wherein $R^a$ is as defined herein. For example, each of R¹ and R² can be a $C_{1-20}$ alkyl group, a $C_{1-20}$ haloalkyl group, a $C_{2-20}$ alkenyl group, a $C_{2-20}$ alkynyl group, a $C_{3-14}$ cycloalkyl group, and a 3-14 membered cycloheteroalkyl group, wherein each of the $C_{1-20}$ alkyl group, the $C_{2-20}$ alkenyl group, the $C_{2-20}$ alkynyl group, the $C_{3-14}$ cycloalkyl group, and the 3-14 membered cycloheteroalkyl group, can be optionally substituted with 1-5 $R^a$ groups, wherein $R^a$ is as defined herein. In particular embodiments, each of R¹ and R² can be a straight-chain $C_{3-16}$ alkyl group (e.g., an n-octyl group), a straight-chain $C_{1-20}$ haloalkyl group (e.g., a straight-chain $C_{1-20}$ fluoroalkyl group), a straight-chain $C_{2-20}$ alkenyl group, a straight-chain $C_{2-20}$ alkynyl group, a $C_{3-14}$ cycloalkyl group (e.g., a cyclohexyl group), and a 3-14 membered cycloheteroalkyl group, wherein the $C_{3-14}$ cycloalkyl group and the 3-14 membered cycloheteroalkyl group can be optionally substituted with 1-4 substituents selected from a halogen (e.g., F, Cl, Br, or I), —CN, —NO₂, —N⁺(CH₃)₃, and a $C_{1-6}$ haloalkyl group.

Another aspect of the present teachings relates to optionally N-substituted naphthalene dicarboximides and optionally N-substituted naphthalene bis(dicarboximides), the core of which can be substituted with one or more (e.g., 1-4) electron-withdrawing substituents (other than cyano groups) or moieties including one or more (e.g., 1-5) electron-withdrawing substituent(s) (including cyano groups). Compounds according to these embodiments can have a formula selected from:

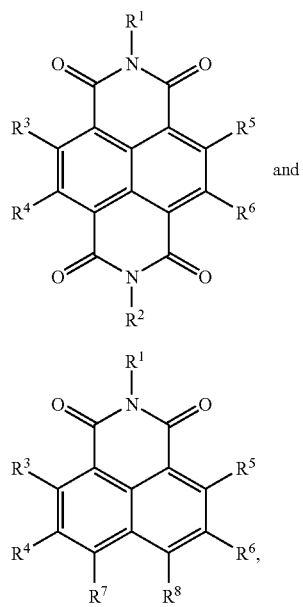

and

IV wherein:

R¹ and R² independently are selected from a) H, b) a $C_{1-20}$ alkyl group, c) a $C_{1-20}$ haloalkyl group, d) a $C_{2-20}$ alkenyl group, e) a $C_{2-20}$ alkynyl group, f) a $C_{3-14}$ cycloalkyl group, g) a $C_{6-14}$ aryl group, h) a 3-14 membered cycloheteroalkyl group, and i) a 5-14 membered heteroaryl group, wherein each of the $C_{1-20}$ alkyl group, the $C_{2-20}$ alkenyl group, the $C_{2-20}$ alkynyl group, the $C_{3-14}$ cycloalkyl group, the $C_{6-14}$ aryl group, the 3-14 membered cycloheteroalkyl group, and the 5-14 membered heteroaryl group is optionally substituted with 1-5 $R^a$ groups;

R³, R⁴, R⁵, and R⁶ are independently selected from a) H, b) a halogen, c) —NO₂, d) —N⁺(R^b)₃, e) —S(O)₂R^b, f) —S(O)₂OR^b, g) —C(O)R^b, h) —C(O)OR^b, i) —(CH₂CH₂O)_n CH₂CH₂OH, j) a $C_{1-20}$ haloalkyl group, k) a $C_{3-14}$ cycloalkyl group, l) a $C_{6-14}$ aryl group, m) a 3-14 membered cycloheteroalkyl group, and n) a 5-14 membered heteroaryl group, wherein each of the $C_{3-14}$ cycloalkyl group, the $C_{6-14}$ aryl group, the 3-14 membered cycloheteroalkyl group, and the 5-14 membered heteroaryl group is optionally substituted with 1-5 $R^a$ groups;

R⁷ and R⁸ are independently selected from a) H), b) a halogen, c) —CN, d) —NO₂, e) —N⁺(R^b)₃, f) —S(O)₂R^b, g) —S(O)₂OR^b, h) —C(O)R^b, i) —C(O)OR^b, j) —(CH₂CH₂O)_n CH₂CH₂OH, k) a $C_{1-20}$ haloalkyl group, l) a $C_{3-14}$ cycloalkyl group, m) a $C_{6-14}$ aryl group, n) a 3-14 membered cycloheteroalkyl group, and o) a 5-14 membered heteroaryl group, wherein each of the $C_{3-14}$ cycloalkyl group, the $C_{6-14}$ aryl group, the 3-14 membered cycloheteroalkyl group, and the 5-14 membered heteroaryl group is optionally substituted with 1-5 $R^a$ groups;

$R^a$, at each occurrence, is independently selected from a) a halogen, b) —CN, c) —NO$_2$, d) —N$^+$(R$^b$)$_3$, e) —S(O)$_m$R$^b$, f) —S(O)$_m$OR$^b$, g) —C(O)R$^b$, h) —C(O)OR$^b$, i) —(CH$_2$CH$_2$O)$_n$CH$_2$CH$_2$OH, and j) a C$_{1-20}$ haloalkyl group;

$R^b$, at each occurrence, is independently selected from a) H, b) a C$_{1-20}$ alkyl group, c) a C$_{1-20}$ haloalkyl group, d) a C$_{6-14}$ aryl group, e) a —(C$_{1-20}$ alkyl)-C$_{6-14}$ aryl group, and f) a —(C$_{1-20}$ haloalkyl)-C$_{6-14}$ aryl group;

m is 0, 1 or 2; and n is 1, 2, 3, 4, 5, 6, 7, 8, 9 or 10;

provided that at least one of $R^3$, $R^4$, $R^5$, and $R^6$ is not H.

Similar to compounds of formula I or II, in some embodiments of compounds of formula III or IV, $R^1$ and $R^2$ independently can be selected from a C$_{1-20}$ alkyl group, a C$_{1-20}$ haloalkyl group, a C$_{2-20}$ alkenyl group, a C$_{2-20}$ alkynyl group, a C$_{3-14}$ cycloalkyl group, a C$_{6-14}$ aryl group, a 3-14 membered cycloheteroalkyl group, and a 5-14 membered heteroaryl group, wherein each of the C$_{1-20}$ alkyl group, the C$_{2-20}$ alkenyl group, the C$_{2-20}$ alkynyl group, the C$_{3-14}$ cycloalkyl group, the C$_{6-14}$ aryl group, the 3-14 membered cycloheteroalkyl group, and the 5-14 membered heteroaryl group can be optionally substituted with 1-5 $R^a$ groups, wherein $R^a$ is as defined herein. For example, each of $R^1$ and $R^2$ can be a C$_{1-20}$ alkyl group, a C$_{1-20}$ haloalkyl group, a C$_{2-20}$ alkenyl group, a C$_{2-20}$ alkynyl group, a C$_{3-14}$ cycloalkyl group, and a 3-14 membered cycloheteroalkyl group, wherein each of the C$_{1-20}$ alkyl group, the C$_{2-20}$ alkenyl group, the C$_{2-20}$ alkynyl group, the C$_{3-14}$ cycloalkyl group, and the 3-14 membered cycloheteroalkyl group, can be optionally substituted with 1-5 $R^a$ groups, wherein $R^a$ is as defined herein. In particular embodiments, each of $R^1$ and $R^2$ can be a straight-chain C$_{3-16}$ alkyl group (e.g., an n-octyl group), a straight-chain C$_{1-20}$ haloalkyl group (e.g., a straight-chain C$_{1-20}$ fluoroalkyl group), a straight-chain C$_{2-20}$ alkenyl group, a straight-chain C$_{2-20}$ alkynyl group, a C$_{3-14}$ cycloalkyl group (e.g., a cyclohexyl group), and a 3-14 membered cycloheteroalkyl group, wherein the C$_{3-14}$ cycloalkyl group and the 3-14 membered cycloheteroalkyl group can be optionally substituted with 1-4 substituents selected from a halogen (e.g., F, Cl, Br, or I), —CN, —NO$_2$, —N$^+$(CH$_3$)$_3$, and a C$_{1-6}$ haloalkyl group.

In certain embodiments of compounds of formula III or IV, at least one of $R^3$, $R^4$, $R^5$, and $R^6$ can be selected from a halogen (e.g., F, Cl, Br, or I), —NO$_2$, —N$^+$(R$^b$)$_3$, —S(O)$_2$R$^b$, —S(O)$_2$OR$^b$, —C(O)R$^b$, —C(O)OR$^b$, —(CH$_2$CH$_2$O)$_n$CH$_2$CH$_2$OH, and a C$_{1-20}$ haloalkyl group, wherein $R^b$ and n are as defined herein. In particular embodiments, each of $R^4$ and $R^5$ can be selected from a halogen (e.g., Br), —NO$_2$, —N$^+$(R$^b$)$_3$, —S(O)$_2$R$^b$, —S(O)$_2$OR$^b$, —C(O)R$^b$, —C(O)OR$^b$, —CH$_2$CH$_2$O)$_n$CH$_2$CH$_2$OH, and a C$_{1-20}$ haloalkyl group, wherein $R^b$ and n are as defined herein. In various embodiments of compounds of formula IV, $R^7$ and $R^8$ independently can be H or CN.

Compounds of formula I and II can be prepared from various naphthalene dicarboxylic anhydrides or amines (or tetracarboxylic dianhydrides or diamines), wherein the core of these precursors can be substituted with one or more leaving groups. Examples of such leaving groups can include, without limitation, halide (e.g., Cl, Br, I), azide (N3), thiocyanate (SCN), nitro (NO$_2$), tosylate (toluenesulfonate, TsO), mesylate (methanesulfonate, MsO), brosylate (p-bromobenzenesulfonate, BsO), nosylate (4-nitrobenzenesulfonate, NsO), and triflate (trifluoromethanesulfonate, OTf).

More specifically, and using the preparation of NN'-bis(n-octyl)-2,6-dicyanonaphthalene-1,4,5,8-bis(dicarboximide) (NDI-8CN$_2$) to illustrate, compounds of formula I or II can be prepared generally according to Scheme 1 below, where a) is Br$_2$/I$_2$ and oleum, b) is n-octylamine and HOAc, and c) is CuCN and DMF.

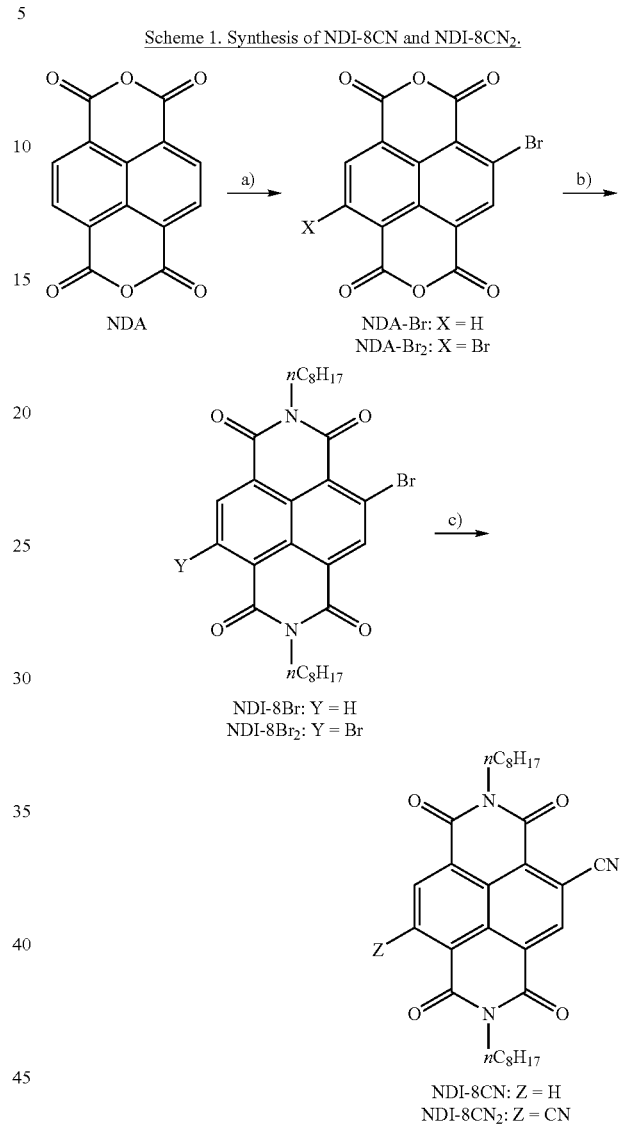

Scheme 1. Synthesis of NDI-8CN and NDI-8CN$_2$.

Previously, the bromination of naphthalene dianhydride (NDA) was accomplished by reaction with Br$_2$ and I$_2$ in oleum and reported to give an inseparable mixture of the mono-, di-, and tri-brominated species. Previous reports describing the synthesis of a complex mixture of chlorinated NDAs from pyrene are known, but it was found that a readily available Br$_2$/I$_2$/oleum mixture can be used to core-brominate NDA. Using the conditions described in Scheme 1, the reaction proceeds in respectable yields without evidence of multiple bromination patterns, as seen in the crystal structure of NDI-8Br$_2$ (FIGS. 1a-b), in contrast to using brominated perylene dianhydride or chlorinated naphthalene dianhydride.

NDI-8CN$_2$ was characterized to demonstrate the high mobility and air stability of the compounds of the present teachings among other various desirable properties. In particular, solution-phase molecular characterization of NDI-8CN$_2$ was accomplished using electrochemistry and optical absorption/emission spectroscopy. Cyclic voltammetry in dichloromethane revealed a first reduction potential of +0.08 V versus SCE, which is approximately 0.5 V easier to reduce than the uncyanated naphthalene diimide analogue (N,N'-bis(n-octyl)-naphthalene-1,4,5,8-bis(dicarboximide), NDI-8) and slightly more positive than that of N,N'-bis(cyclohexyl)-1,7-dicyano-perylene-3,4,9,10-bis(dicarboximide). For N,N'-bis(n-octyl)-2-cyanonaphthalene-1,4,5,8-bis(dicarboximide) (NDI-8CN), the first reduction potential was determined to be −0.22 versus SCE.

Figure 2:
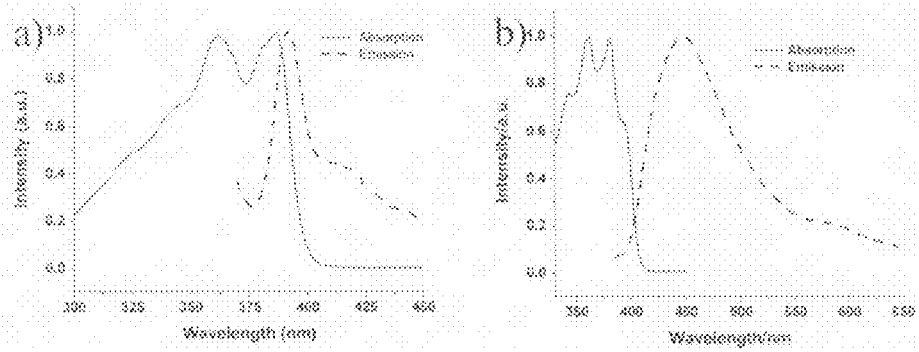
FIGS. 2a-b show the optical absorption and emission spectra of two representative compounds according to the present teachings, in particular, NDI-8CN (FIG. 2a) and NDI-8CN$_2$ (FIG. 2b) in dichloromethane.

The optical absorption spectra of NDI-8CN and NDI-8CN$_2$ (FIG. 2) showed minimal differences relative to the unsubstituted naphthalene diimide (NDI-8) with absorption maxima at 380 nm, and 361 nm, while the steady-state fluorescence revealed an emission maximum at 447 nm ($\lambda_{ex}$=350 nm).

The absolute NDI-8CN$_2$ molecular orbital energies were estimated from E$_{red1}$ and the optical bandgap to be −4.5 eV and −7.5 eV for the LUMO and HOMO, respectively. Interestingly, the wide band gap of ~3.0 eV (415 nm) makes this material nearly transparent in the visible region.

The present compounds (e.g., NDI-8CN and NDI-8CN$_2$) can be used to prepare a thin film semiconductor. Various thin film deposition techniques can be employed including, but not limited to, vapor deposition and various solution-phase processing techniques. Certain compounds of the present teachings can have satisfactory solubilities in common organic solvents, making them suitable for use in various solution-phase processes (e.g., printing, spin coating, drop-casting, dip coating, and blade coating). Examples of common organic solvents include, but are not limited to, petroleum ethers; aromatic hydrocarbons such as benzene, toluene, xylene, and mesitylene; ketones, such as acetone, and 2-butanone; ethers, such as tetrahydrofuran, dioxane, bis(2-methoxyethyl)ether, and diethyl ether; alcohols, such as isopropyl alcohol; aliphatic hydrocarbons, such as hexanes; acetates, such as ethyl acetate; and halogenated aliphatic hydrocarbons, such as dichloromethane, chloroform, and ethylene chloride. As used herein, a compound can be considered soluble in a solvent when at least 1 mg of the compound is soluble in 1 mL of the solvent.

Figure 3:
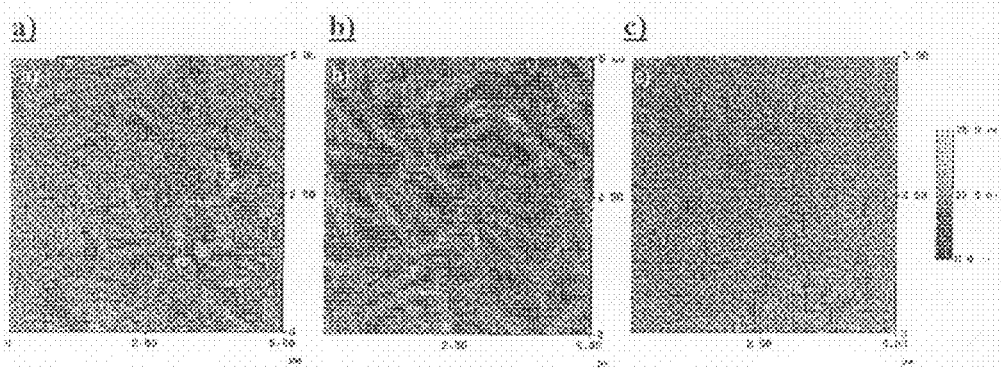
FIGS. 3a-c show the atomic force microscopy (AFM) images of 100 nm thick NDI-8CN$_2$ films deposited on a SiO$_2$ substrate (FIG. 3a), an HMDS substrate (FIG. 3b), and a polystyrene (PS) substrate (FIG. 3c). The polycrystalline ribbon-like surface morphology is similar in the SiO$_2$ and HMDS films, while the PS film has smaller features of the same general shape.

Vapor-deposited films of NDI-8CN and NDI-8CN$_2$ were characterized by optical absorption spectroscopy, atomic force microscopy (AFM), x-ray diffraction (XRD), and OFET measurements. Furthermore, top-contact OFETs were evaluated under multiple semiconductor growth/device fabrication conditions by varying the dielectric/thin film surface treatment, substrate temperature during deposition of the semiconductor materials, and atmosphere during OFET measurement. The performance of NDI-8CN OFETs and NDI-8CN$_2$ OFETs was evaluated on multiple substrates by varying the treatment of the dielectric from O$_2$ plasma cleaning (SiO$_2$), to 1,1,1,3,3,3-hexamethyldisilazane vapor (HMDS), to spin-cast polystyrene (PS). Devices on these different substrates maintained at 90° C. during growth were fabricated by simultaneous deposition of a 100 nm thick semiconductor film at 0.4 Å/s (Table 1). The devices fabricated on untreated SiO$_2$ substrates were observed to have comparable or slightly higher mobilities than those treated with HMDS which, without wishing to be bound by any particular theory, is believed to be due to imperfections in the chemically applied HMDS-derived monolayer providing a less uniform interface. Interestingly, the comparable NDI-8CN$_2$ mobility of untreated and HMDS-treated dielectric devices suggests that the NDI-8CN$_2$ conducting orbitals are lower in energy than the silanol-based traps that are known to hinder n-type charge transport in some semiconductors with lower electron affinity. The electrical performance of PS substrates shows a more dramatic decrease, presumably due to the small sized crystal grains as measured by AFM (see FIG. 3c). AFM of HMDS and SiO$_2$ reveals comparable crystalline surface morphology (FIGS. 3a-b).

TABLE 1

Electrical properties of NDI-8CN$_2$ FETs in vacuum and in air on different substrates.

| Substrate | $\mu^{vac}$ (cm$^2$V$^{-1}$s$^{-1}$) | I$_{on}$/I$_{off}^{vac}$ | V$_{IH}^{vac}$ (V) | $\mu^{air}$ (cm$^2$V$^{-1}$s$^{-1}$) | I$_{on}$/I$_{off}^{air}$ | V$_{IH}^{air}$ (V) |
|---|---|---|---|---|---|---|
| SiO$_2$ | 4 × 10$^{-2}$ | 10$^4$ | −3(1) | 4 × 10$^{-2}$ | 10$^5$ | +4(5) |
| HMDS | 3 × 10$^{-2}$ | 10$^5$ | −1(7) | 2 × 10$^{-2}$ | 10$^5$ | +11(14) |
| PS | 6(3) × 10$^{-3}$ | 10$^2$ | −46(16) | 7(2) × 10$^{-3}$ | 10$^2$ | −34(21) |

I$_{on}$/I$_{off}$ values are for gate bias ranging from −100 V to +100 V.

Figure 4:
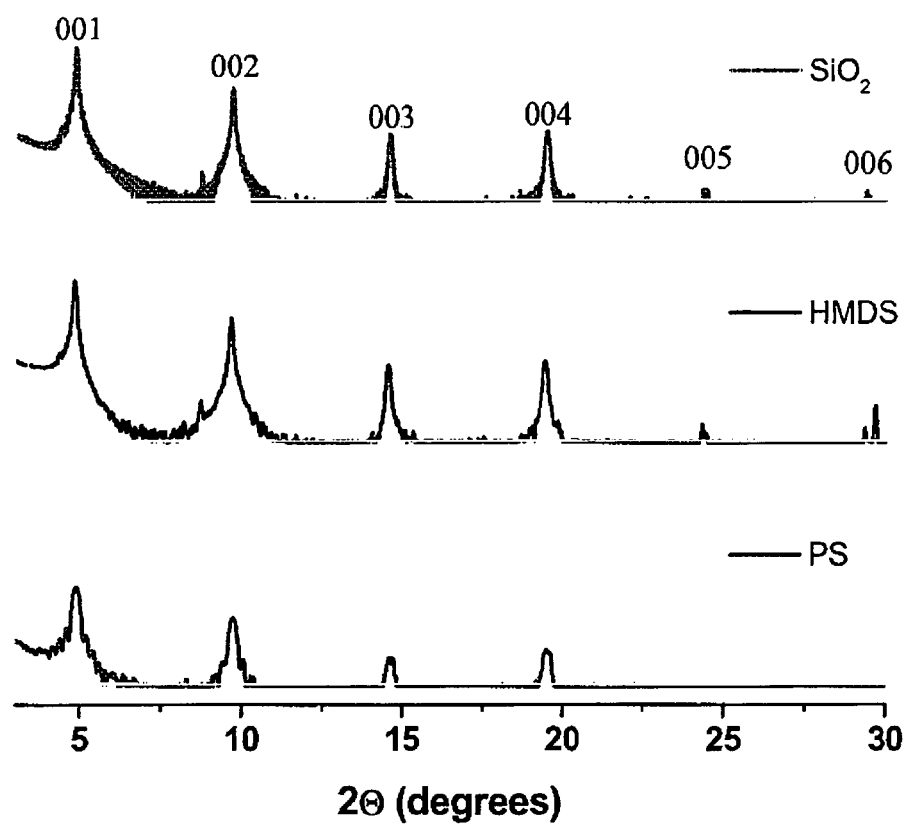
FIG. 4 shows the Θ/2Θ x-ray diffraction (XRD) scans of 100 nm NDI-8CN$_2$ films deposited simultaneously onto bare SiO$_2$, HMDS-treated SiO$_2$, and spin-cast polystyrene (PS) substrates. The 005 and 006 peaks are absent for films of the same thickness on PS substrates.
Figure 5:
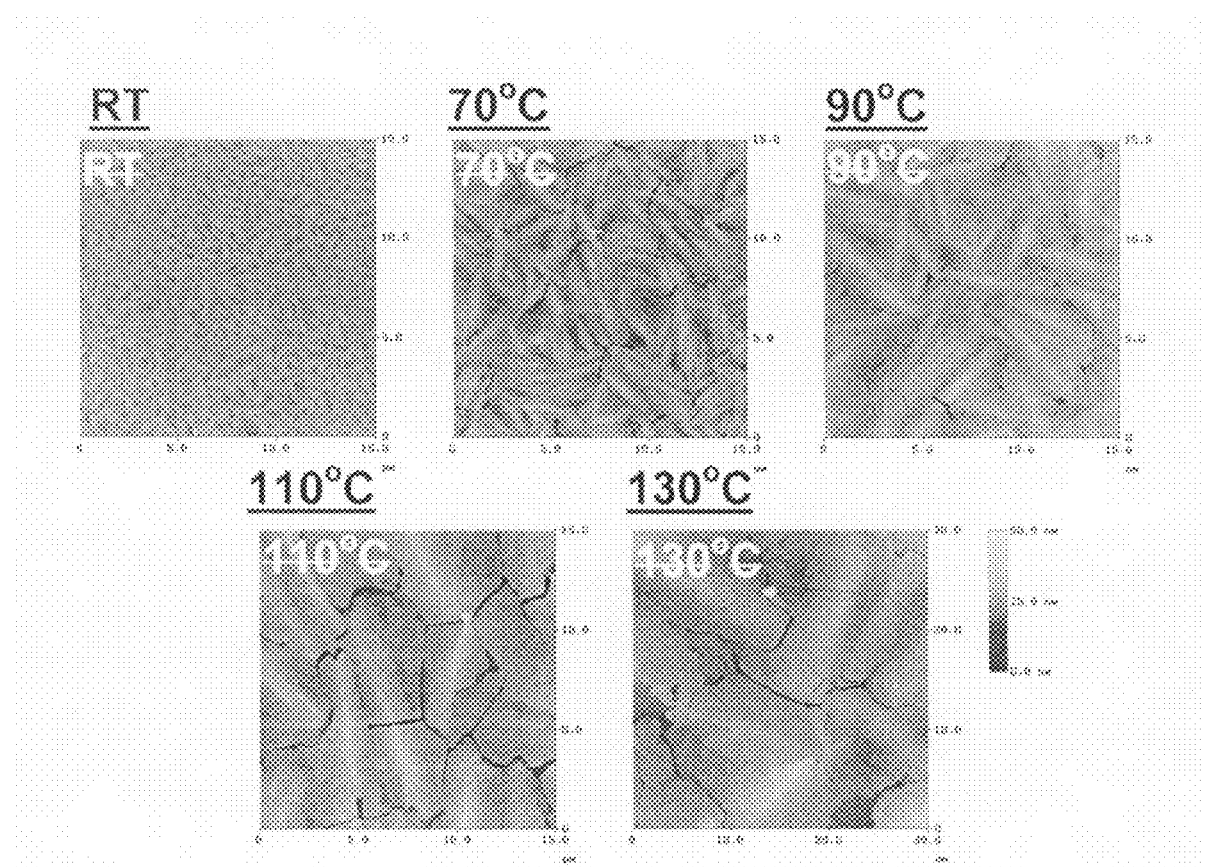
FIG. 5 shows the tapping-mode AFM images of 50 nm NDI-8CN films deposited at 0.2 Å/s onto n$^+$-Si/SiO$_2$ substrates held at the indicated deposition temperature (T$_d$) (i.e., at room temperature, 70° C., 90° C., 110° C., and 130° C., respectively).
Figure 6:
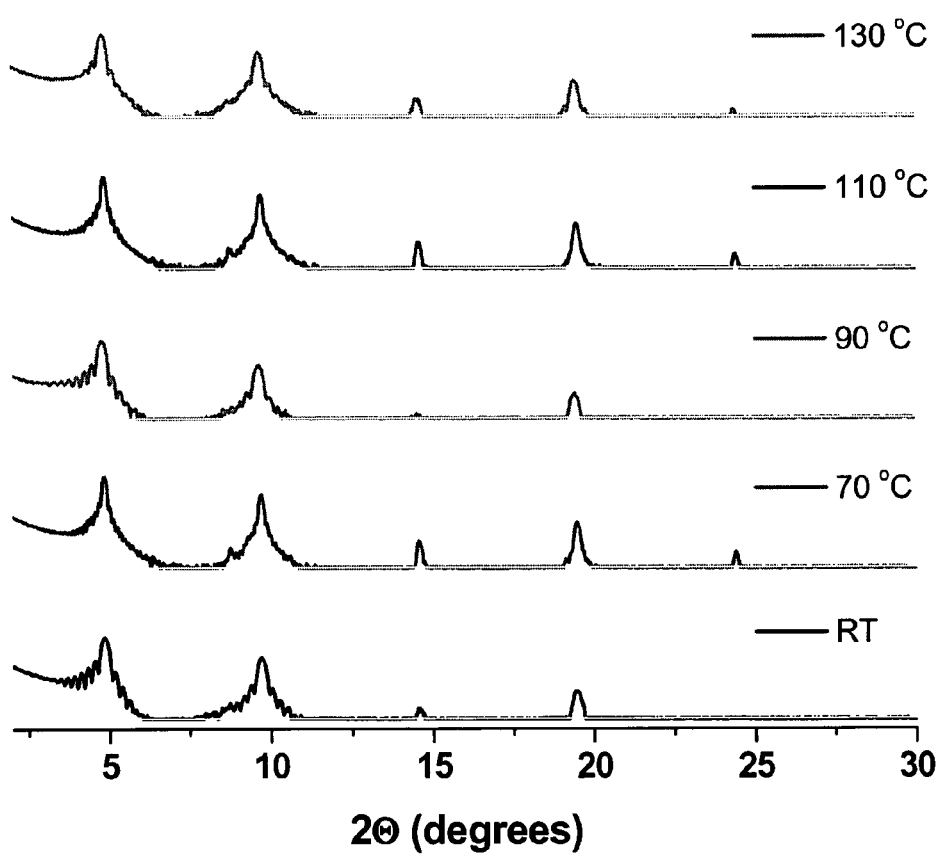
FIG. 6 shows the Θ/2Θ XRD scans of 50 nm NDI-8CN films deposited at 0.2 Å/s onto a n$^+$-Si/SiO$_2$ substrates held at the indicated T$_d$ (i.e., at room temperature, 70° C., 90° C., 110° C., and 130° C., respectively).
Figure 7:
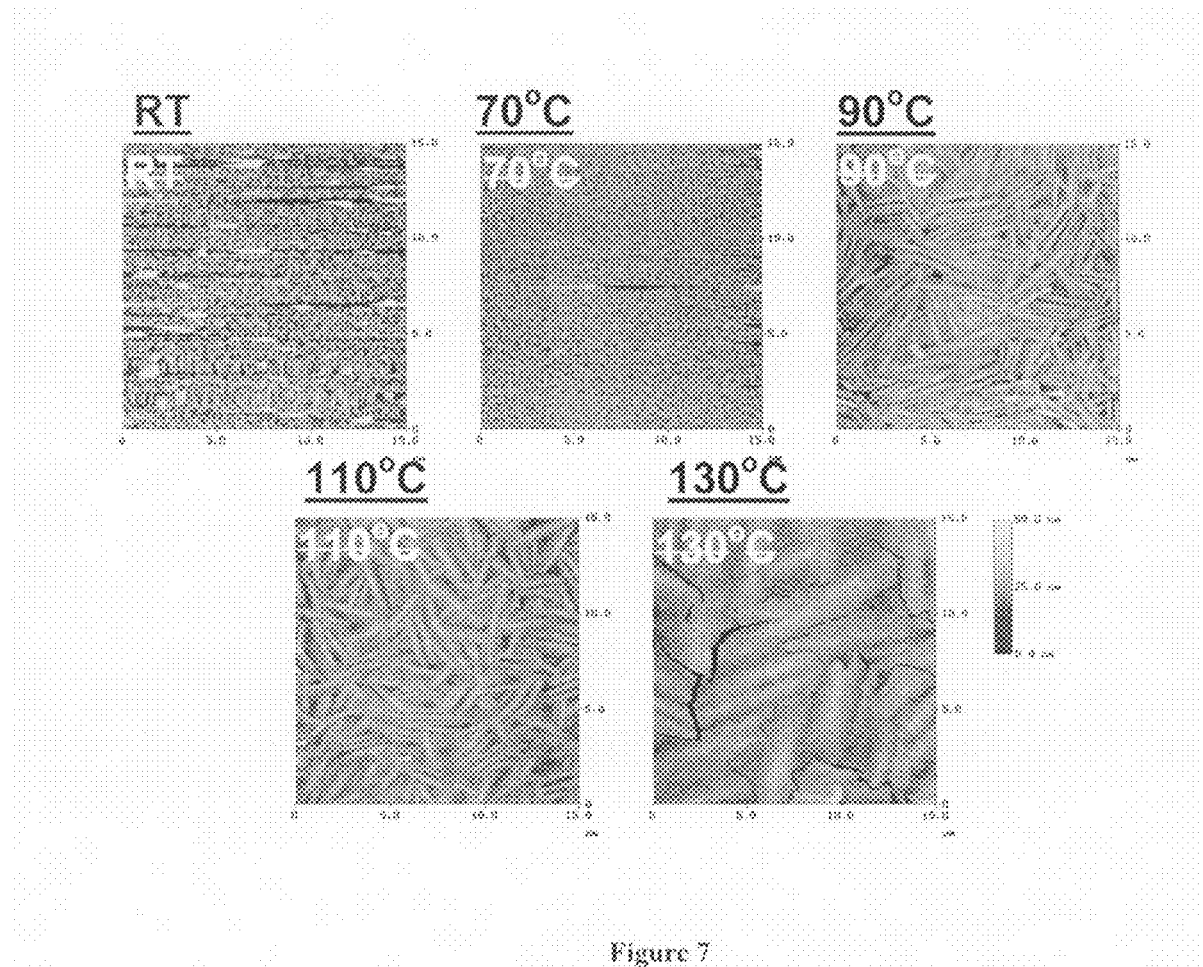
FIG. 7 shows the tapping-mode AFM images of 50 nm NDI-8CN$_2$ films deposited at 0.2 Å/s onto n$^+$-Si/SiO$_2$ substrates held at the indicated T$_d$ (i.e., at room temperature, 70° C., 90° C., 110° C., and 130° C., respectively).
Figure 8:
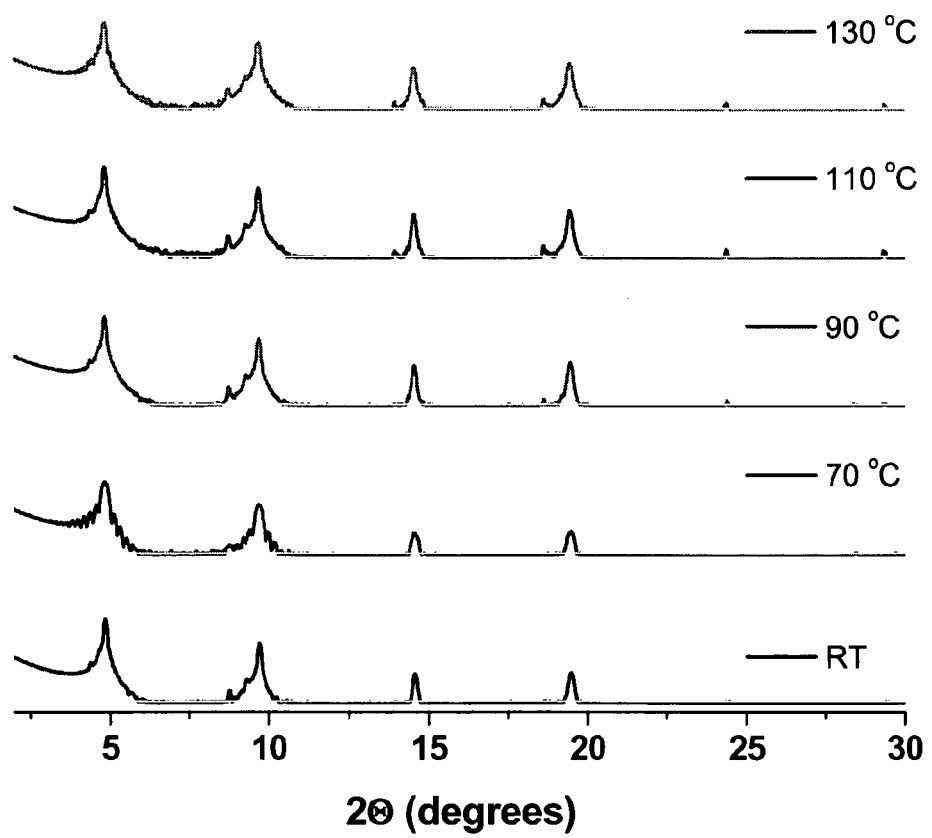
FIG. 8 shows the Θ/2Θ XRD scans of 50 nm NDI-8CN$_2$ films deposited at 0.2 Å/s onto a n$^+$-Si/SiO$_2$ substrates held at the indicated T$_d$ (i.e., at room temperature, 70° C., 90° C., 110° C., and 130° C., respectively).
Figure 9:
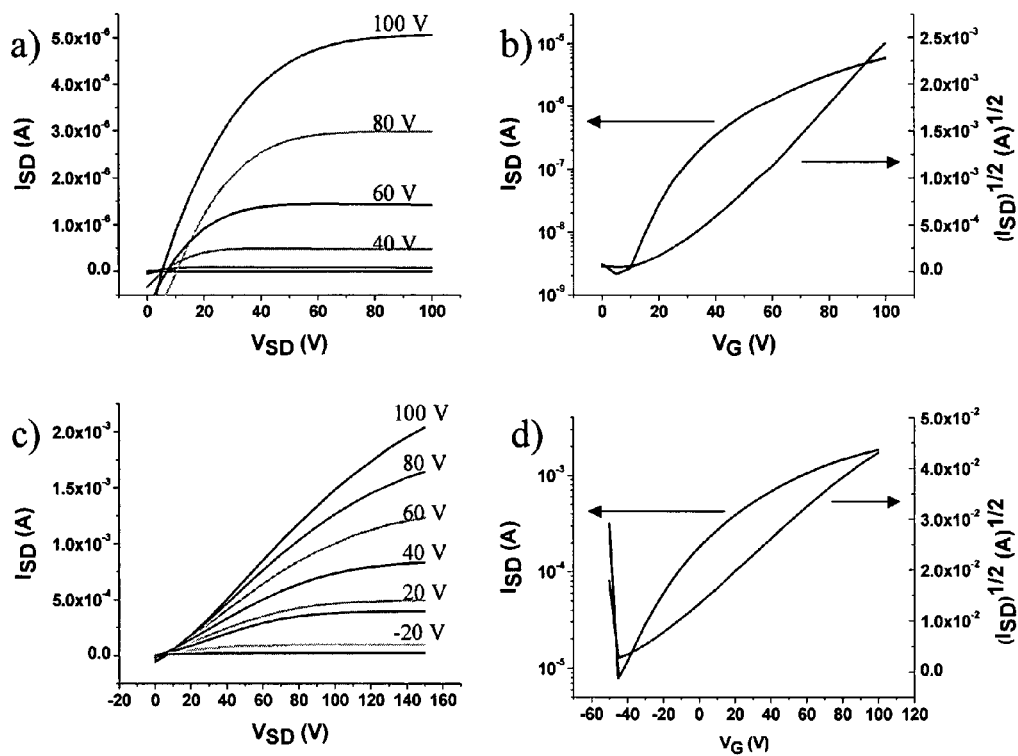
FIGS. 9a-d illustrate the typical I-V characteristics measured under vacuum of an NDI-8CN device (FIG. 9a: output plots at 0 V, 20 V, 40 V, 60 V, 80 V, and 100V.
Figure 10:
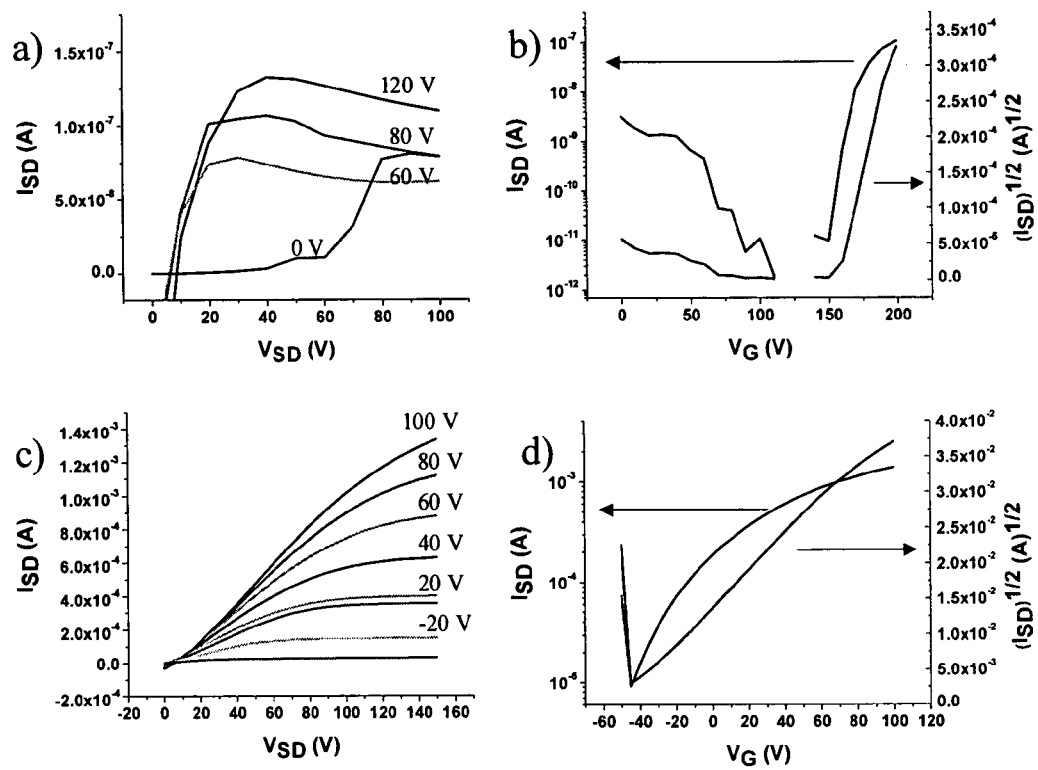
FIGS. 10a-d illustrate the typical I-V characteristics measured in air of an NDI-8CN organic field-effect transistor (OFET) device (FIG. 10a: output plots at 0 V, 40 V, 80 V, and 120V.

XRD experiments reveal that all NDI-8CN$_2$ films are polycrystalline with a d-spacing ~18.2 Å. The derived layered structure with the long-axis ~45° to the substrate perpendicular indicates that the molecules are aligned in an efficient direction for charge transport between source and drain. Independent of the dielectric surface treatment, all films have a high degree of long range ordering as indicated by multiple diffraction peaks and Laue oscillations around the first order diffraction; however, the SiO$_2$ and HMDS films exhibit up to 6 reflections versus 4 for PS (FIG. 4). The out-of-plane texture is better in the SiO$_2$ and HMDS cases compared to PS, as indicated by the rocking curves with the full width values at half maximum (FWHMs) of 0.03° and 005°, respectively.

The temperature of the substrate during deposition of the semiconductor layer was next investigated on SiO$_2$ substrates (FIGS. 5-8). The optimal conditions were found for deposition of NDI-8CN and NDI-8CN$_2$ (0.2 Å/s, 50 nm thick) onto a substrate at temperatures between 90-130° C., the latter yielding top-contact devices with a mobility of ~0.2 cm$^2$V$^{-1}$s$^{-1}$ I$_{on}$/I$_{off}$=10$^3$ (V$_G$=−100V/100 V), and V$_{TH}$ ~0 V. Interestingly, the only noticeable difference in electrical parameters between NDI-8CN$_2$ and the previously reported uncyanated derivative NDI-8 is a decrease in V$_{TH}$, which reflects the higher electron affinity of NDI-8CN$_2$. The similar mobilities of NDI-8 and NDI-8CN$_2$ suggest that the addition of the cyano groups does not significantly affect the coupling between molecules which is dictated by NDI core packing (see FIG. 1c).

The electrical properties of an NDI-8CN device and an NDI-8CN$_2$ device according to the present teachings were investigated and compared while operated under vacuum (10$^{-4}$ Torr) and ambient atmosphere. FIGS. 9a-b and 10a-b are the output plots and transfer plots of a representative NDI-8CN device operated under vacuum (FIG. 9) and in air (FIG. 10), respectively. FIGS. 9c-d and 10c-d are the output plots and transfer plots of a representative NDI-8CN$_2$ device operated under vacuum (FIG. 9) and in air (FIG. 10), respectively. Comparing the NDI-8CN$_2$ devices operated under vacuum and ambient atmosphere, the electrical properties of the NDI-8CN$_2$ FETs remain similar with the exception of slightly larger threshold voltages in air (see also Tables 2-4). Without wishing to be bound by any particular theory, it is believed that such exceptions were due to an increase in O$_2$-based traps. Such evidence of O$_2$ inclusion into the film combined with the air-stability of the devices suggests that the mechanism for electron stabilization can be mainly due to the low-lying LUMO energy position rather than fluorocarbon kinetic barriers to O$_2$ penetration, as invoked in other air-stable fluorinated naphthalene diimides. Given the air-stability of these devices, all other OFET measurements were performed in ambient atmosphere.

TABLE 2

Average OFET parameters measured under vacuum (10$^{-6}$ Torr) for NDI-8CN devices fabricated with films deposited at the indicated T$_d$. If the standard deviation is less than 5%, it is not given.

| T$_d$ (° C.) | μ (cm$^2$V$^{-1}$s$^{-1}$) | V$_{th}$ (V) | I$_{on}$/I$_{off}$ |
|---|---|---|---|
| 23  | 9.9 × 10$^{-4}$ | 35 (4)  | 10$^5$ |
| 70  | 2.2 × 10$^{-3}$ (4 × 10$^{-4}$) | 53 (10) | 10$^4$ |
| 90  | 3.7 × 10$^{-3}$ (4 × 10$^{-4}$) | 34 (4)  | 10$^5$ |
| 110 | 2.5 × 10$^{-3}$ | 39 (2)  | 10$^5$ |
| 130 | 4.7 × 10$^{-3}$ (2 × 10$^{-4}$) | 28 (2)  | 10$^5$ |

TABLE 3

Average OFET parameters measured under vacuum (10$^{-6}$ Torr) for NDI-8CN$_2$ devices fabricated with films deposited at the indicated T$_d$. If the standard deviation is less than 5%, it is not given.

| T$_d$ (° C.) | μ (cm$^2$V$^{-1}$s$^{-1}$) | V$_{th}$ (V) | I$_{on}$/I$_{off}$ |
|---|---|---|---|
| 23  | 6.9 × 10$^{-2}$ (2 × 10$^{-3}$) | -32 (2) | 10$^2$ |
| 70  | 3.6 × 10$^{-3}$ | 13 (3)  | 10$^3$ |
| 90  | 0.12 (0.007) | -10 (1) | 10$^3$ |
| 110 | 0.15 (0.01)  | -37 (2) | 10$^2$ |
| 130 | 0.14 | -37 (2) | 10$^2$ |

TABLE 4

Average OFET parameters measured under air for NDI-8CN$_2$ devices fabricated with films deposited at the indicated T$_d$. If the standard deviation is less than 5%, it is not given.

| T$_d$ (° C.) | μ (cm$^2$V$^{-1}$s$^{-1}$) | V$_{th}$ (V) | I$_{on}$/I$_{off}$ |
|---|---|---|---|
| 23  | 4.8 × 10$^{-2}$ | -28 (1) | 10$^2$ |
| 70  | 8.4 × 10$^{-2}$ (6 × 10$^{-3}$) | -11 (2) | 10$^2$ |
| 90  | 0.11 (0.004) | 10 (1)  | 10$^4$ |
| 110 | 0.11 (0.01)  | -55 (5) | 10$^3$ |
| 130 | 0.09 | -39 (1) | 10$^3$ |

Figure 11:
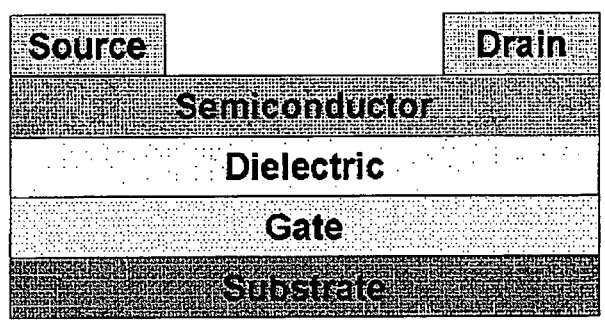
FIG. 11 illustrates a general organic thin film transistor (OTFT) device structure incorporating semiconductor materials prepared from one or more of the present compounds.

Given the transparency in the visible of NDI-8CN$_2$ films, the fabrication of the first transparent n-type organic transistor was achieved. The use of wide-band gap NDI-8CN$_2$ as the active layer eliminates the absorptive contribution of the semiconducting material. Hence, by using transparent electrodes and dielectric materials, entirely transparent devices in any electrode configuration can be fabricated. The general field-effect transistor device structure is shown in FIG. 11. Suitable materials for the source, drain, and gate electrodes include, without limitation, metals (e.g., Au, Al, Ni, Cu), transparent conducting oxides (e.g., ITO, IZO, ZITO, GZO, GIO, GITO), and conducting polymers (e.g., poly(3,4-ethylenedioxythiophene) poly(styrenesulfonate) (PEDOT:PSS), polyaniline (PANI), polypyrrole (PPy)). Suitable dielectric materials include, without limitation, inorganic oxides (e.g., SiO$_2$, Al$_2$O$_3$, HfO$_2$), polymers (e.g., the crosslinked polymer blends described in U.S. patent application Ser. Nos. 11/315,076, 60/816,952, and 60/861,308, each of which is incorporated by reference herein in its entirety), and a self-assembled superlattice/self-assembled nanodielectric (SAS/SAND) as described in Yoon, M-H. et al., *PNAS*, 102 (13): 4678-4682 (2005), which is incorporated by reference herein in its entirety.

Figure 12:
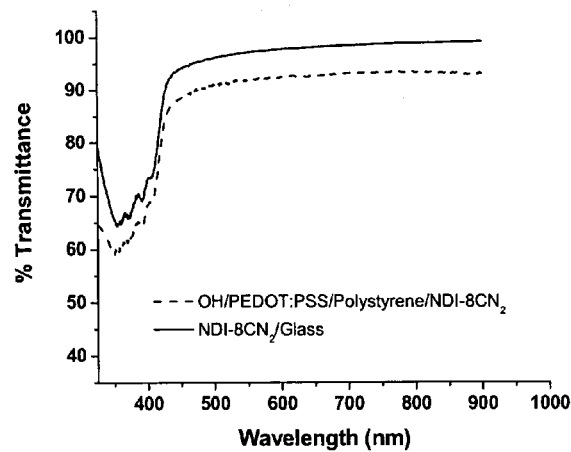
FIG. 12 shows the transmittance spectra of an NDI-8CN$_2$ film on glass and an OFET channel with an overhead transparency film as the substrate, PEDOT:PSS (1:1) as the gate, polystyrene as the dielectric, and NDI-8CN$_2$ as the semiconducting layer. Greater than 90% transmittance over the range of 425-800 nm was observed, indicating that these films are almost entirely transparent in the visible spectrum.
Figure 13:
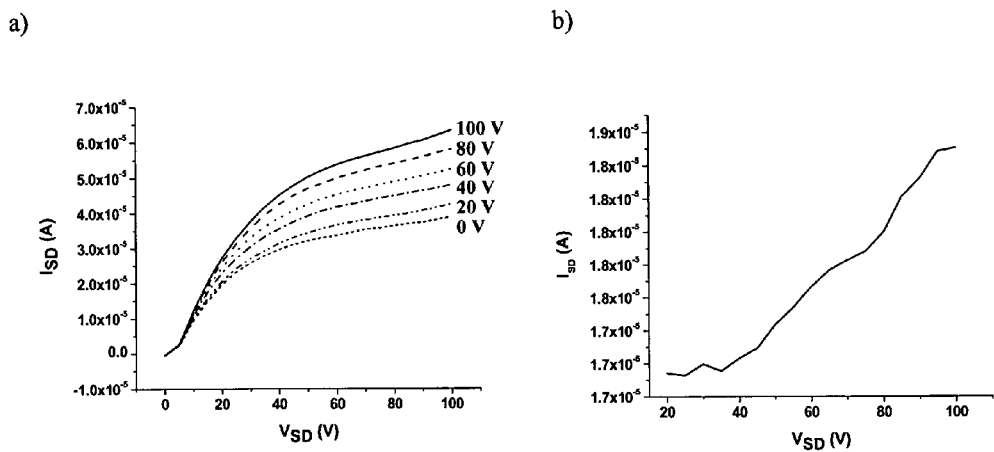
FIGS. 13a-b shows the I-V characteristics of a top-contact OFET with the device structure as follows: overhead transparency (substrate), PEDOT:PSS (gate), polystyrene (dielectric), NDI-8CN$_2$ (semiconductor), and Au (source/drain). The output characteristics (FIG. 13a) and transfer plot (FIG. 13b) illustrate current modulation in this device.
Figure 14:
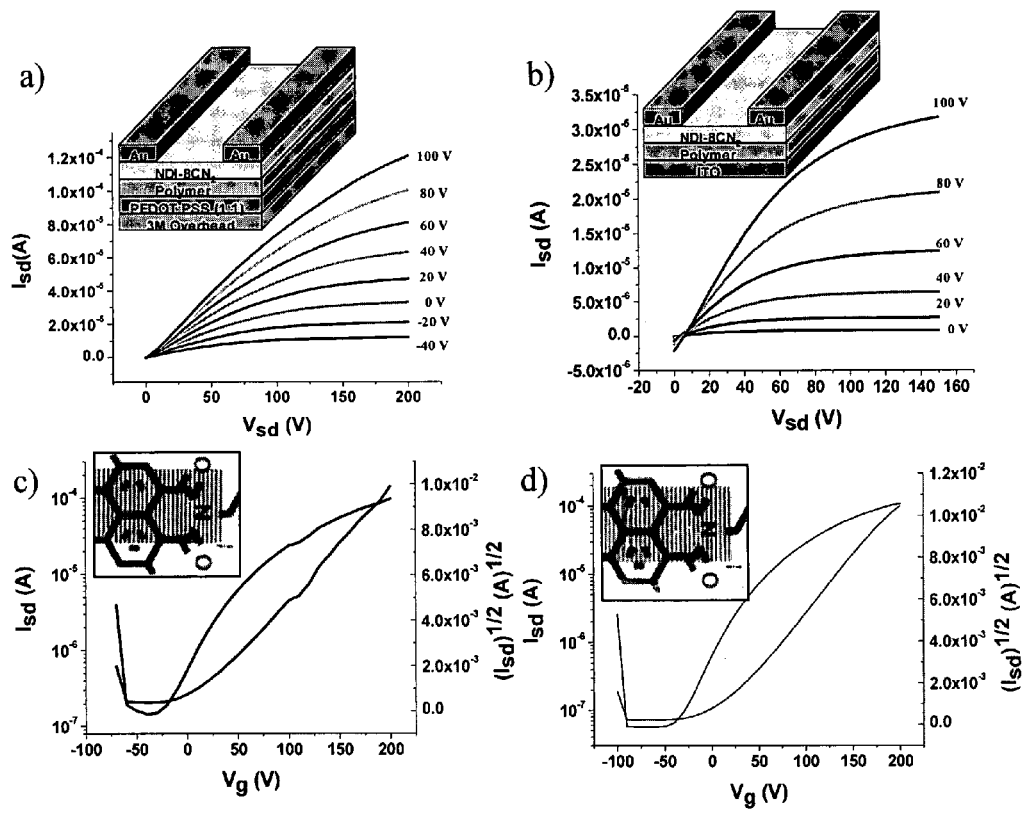
FIGS. 14a-d show the OFET data for two representative transparent air-stable n-channel devices, each of which incorporates a semiconductor layer prepared from a compound of the present teachings (e.g., NDI-8CN$_2$).

For example, a transparent n-channel OFET can be fabricated with NDI-8CN$_2$ in the following manner. The transparent device was fabricated on a 3M overhead transparency film cut into 3 cm×1.5 cm rectangles, followed by cleaning with H$_2$O, hexanes, and toluene. The substrates were then subjected to a 1 minute plasma cleaning. PEDOT:PSS (1:1) solution purchased from Baytron was spin-cast at 2000 rpm for 45 seconds, followed by annealing in a vacuum oven at 85° C. overnight to yield ~40 nm thin films with a resistance between 5 and 14 MΩ. Polystyrene solutions in toluene (40 mg/1.25 mL) were spin-coated at 2000 rpm for 45 seconds onto the PEDOT:PSS films and dried in an 85° C. vacuum oven overnight. Alternatively, a P-UV-013 dielectric may be used in place of the PS film. NDI-8CN$_2$ films 50 nm thick were then vapor-deposited at 0.2 Å/s onto the polystyrene film held at 70° C. Gold source and drain electrodes were evaporated through a shadow mask to yield air-stable n-channel OFETs with a transparent channel. The transmittance spectrum of the channel and the I-V curves of representative and analogous devices are presented in FIGS. 12-14.

The following examples are provided to illustrate further and to facilitate the understanding of the present teachings and are not in any way intended to limit the invention.

EXAMPLES $^1$H NMR spectra were recorded on a Varian 400 MHz NMR spectrometer using TMS as an internal standard. Laser desorption mass spectra were obtained with a Perseptive BioSystems time-of-flight MALDI mass spectrometer using a dithranol matrix. Solvents and reagents were used as received. Flash and thin-layer chromatography was performed using Sorbent Technologies (Atlanta, Ga.) silica gel. All solvents were of spectrophotometric grade. Toluene was purified by CuO and alumina columns (GlassContour).

Optical absorption measurements were made on a Shimadzu UV-1601 spectrophotometer using 1.0 cm path length cuvettes. Fluorescence spectra were obtained on a PTI photon-counting spectrofluorimeter.

Electrochemical measurements were performed using a CH Instruments Model 660A electrochemical workstation. The solvent was dichloromethane containing 0.1 M tetra-n-butylammonium hexafluorophosphate electrolyte. A 1.0 mm diameter platinum disk electrode, a platinum wire counter electrode, and a Ag/Ag$_x$O reference electrode were employed. The ferrocene/ferrocinium couple (Fc/Fc$^+$= 0.475v.SCE) was used as an internal reference for all measurements.

Example 1

Preparation of 2,6-dibromonaphthalene-1,4,5,8-tetra-carboxylic dianhydride (NDA-Br$_2$) and 2-bromonaphthalene-1,4,5,8-tetracarboxlic ydianhydride (NDA-Br)

To a 500 mL round-bottom flask was added 19.8 g (73.8 mmol) of naphthalene 1,2,5,6-tetracarboxylic dianhydride and 400 mL of oleum. The suspension was stirred for 3 hours, followed by the addition of 0.812 g (3.20 mmol) of I$_2$. Stirring was then continued for one more hour. To this reaction mixture, 8.0 mL (156 mmol) of Br$_2$ was added dropwise over 15 minutes. The reaction mixture was then heated to 95° C. under N$_2$ for 24 hours and then allowed to cool to room temperature. Next, 600 mL of ice water was added to a 2 L beaker, and the reaction mixture was slowly poured into the ice water. The resulting yellow precipitate was collected by filtration, washed thrice with 15 mL of MeOH, and dried under vacuum to yield 24.1 g of the crude product. This product was sufficiently pure for subsequent synthetic steps. NDA-Br$_2$: MALDI-TOF-MS 426.91 (calcd 425.97). NDA-Br: MALDI-TOF-MS 347.52 (calcd 347.07).

Example 2

Preparation of N,N'-bis(n-octyl)-2,6-dibromonaphthalene-1,4,5,8-tetracarboxylic diimide (NDI-8Br$_2$)

To a 250 mL round-bottom flask was added 2.175 g (5.11 mmol) of 2,6-dibromonaphthalene-1,4,5,8-tetracarboxylic dianhydride (NDA-Br$_2$), 100 mL of N-methyl pyrrolidone, 50 mL of glacial acetic acid, and 8.2 mL (81 mmol) of n-octylamine. The reaction mixture was stirred at 85° C. under N$_2$ for 6 hours. After cooling to room temperature, the reaction mixture was poured into 250 mL of MeOH and placed in a −10° C. freezer overnight. The resulting precipitate was collected by filtration, washed thrice with 15 mL of MeOH and dried. The crude orange product was then purified by chromatography, eluting with dichloromethane, and the second band collected to give 1.5084 g (2.326 mmol, 46% yield) of a yellow product. $^1$H NMR (CDCl$_3$): δ 8.999 (s, 2H), δ 4.189 (t, 4H), δ 1.8-0.8 (m, 30H). MALDI-TOF-MS: 648.77 (calcd 648.43).

Example 3

Preparation of N,N'-bis(n-octyl)-2-bromonaphthalene-1,4,5,8-bis(dicarboximide) (NDI-8Br) and N,N'-bis(n-octyl)-2,6-dibromonaphthalene-1,4,5,8-bis(dicarboximide) (NDI-8Br$_2$)

To a 250 mL round-bottom flask was added 8.21 g of NDA-Br/NDA-Br$_2$, 300 mL of glacial acetic acid, and 18.0 mL (178 mmol) of n-octylamine. The reaction mixture was heated to reflux under N$_2$ for 20 minutes, allowed to cool overnight, and was then poured into 750 mL of MeOH. The resulting precipitate (9.51 g) was collected by filtration, washed thrice with 25 mL of MeOH, and dried under vacuum. The crude orange product was then purified by chromatography on silica, eluting with 60% dichloromethane/40% hexanes, and the first band was collected to yield 0.543 g (0.839 mmol) of NDI-8Br$_2$ as a yellow product. The second band gave 3.74 g of colorless NDI-8Br (6.57 mmol).

NDI-8Br: $^1$H NMR (CDCl$_3$): δ 8.866 (s, 1H), δ 8.791 (d, 1H J=7.2 Hz), δ 8.740 (d, 1H, J=7.2 Hz), δ 4.128 (t, 2H, J=7.2 Hz), δ 4.108 (t, 2H, J=7.2 Hz), δ 1.673-0.789 (m, 30H). MALDI-TOF-MS: 569.0 (calcd 569.53). Anal. calcd. for C$_{30}$H$_{37}$Br$_1$N$_2$O$_4$: C, 63.27; H, 6.55; N, 4.92. Found: C, 63.07; H, 6.47; N, 4.86.

NDI-8Br$_2$: $^1$H NMR (CDCl$_3$): δ 8.974 (s, 2H), δ 4.165 (t, 4H, J=8.0 Hz), δ 1.714-0.857 (m, 30H). MALDI-TOF-MS: 648.77 (calcd 648.43). Anal. calcd. for C$_{30}$H$_{36}$Br$_2$N$_2$O$_4$: C, 55.57; H, 5.60; N, 4.32. Found: C, 55.51; H, 5.57; N, 4.28.

Example 4

Preparation of N,N'-bis(n-octyl)-2-cyanonaphthalene-1,4,5,8-bis(dicarboximide) (NDI-8CN)

To a 500 mL round-bottom flask was added 2.906 g (32.5 mmol) of CuCN, 2.009 g (3.53 mmol) of NDI-8Br, and 100 mL of dimethylformamide. The reaction mixture was stirred under N$_2$ for 7 hours at 150° C. After the reaction mixture had cooled to room temperature, the solvent was removed using a rotary evaporator. The crude product was then continuously extracted from the reaction mixture with chloroform and purified by chromoatography on silica, eluting with dichloromethane. Two gradient sublimations at ~260° C./10$^{-6}$ Torr were used to further purify the chromatographed material, yielding 0.857 g (1.66 mmol, 47% yield) of NDI-8CN. $^1$H NMR (CDCl$_3$): δ 8.875 (s, 1H), δ 8.818 (s, 2H), δ 4.145 (t, 2H, J=8.8 Hz), δ 4.128 (t, 2H, J=8 Hz), δ 1.2-1.8 (m, 30H). MALDI-TOF-MS: 515.50 (calcd 515.64) Anal. calcd. for C$_{31}$H$_{37}$BrN$_3$O$_4$: C, 72.21; H, 7.23; N, 8.15. Found: C, 72.40; H, 7.21; N, 8.17.

Example 5

Preparation of N,N'-bis(n-octyl)-2,6-dicyanonaphthalene-1,4,5,8-bis(dicarboximide) (7NDI-8CN$_2$)

To a 250 mL round-bottom flask was added 0.741 g (8.28 mmol) of CuCN, 0.258 g (0.40 mmol) of NDI-8Br$_2$, and 50 mL of dimethylformamide. The reaction mixture was stirred under N$_2$ for 7 hours at 150° C. After the reaction mixture had cooled to room temperature, the solvent was removed using a rotary evaporator. The crude product was continuously extracted with chloroform, filtered, and the filtrate evaporated and dried. The resulting solid was purified by chromatography on silica, eluting with dichloromethane. Two gradient sublimations at ~260° C./10$^{-6}$ Torr were used to further purify the chromatographed material, yielding 97.0 mg (0.179 mmol, 45% yield) of NDI-8CN$_2$. $^1$H NMR (CDCl$_3$): δ 9.044 (s, 2H), δ 4.227 (t, 4H, J=8.0 Hz), δ 1.759-0.868 (m, 30H). MALDI-TOF-MS: 541.06 (calcd 540.65) Anal. calcd. for C$_{32}$H$_{36}$N$_4$O$_4$: C, 71.09; H, 6.71; N, 10.36; Found; C, 71.13; H, 6.71; N, 10.32.

Example 6

Thin Film Transistor Device Fabrication

Mobilities were measured in the saturation regime according to the following relationship:

$$(I_{SD})_{sat} = (WC_i/2L)\mu(V_G - VT_{TH})^2$$

where L and W are the device channel length (200 μm) and width (5 mm), respectively, and $C_i$ is the capacitance of the insulator ($1\times10^{-8}$ F). The mobility is μ, $V_{TH}$ is the threshold voltage, and $V_G$ is the gate voltage (S. M. Sze, *Physics of Semiconductor Devices*, John Wiley and Sons: New York, 1985).

Vapor-deposited thin films of NDI-8CN$_2$ were deposited thermally at $10^{-6}$ Torr, and the temperature of the substrate during deposition was controlled with a cartridge heater. The films used in the substrate study were deposited at 0.4 Å s$^{-1}$ to a thickness of 100 nm. The optimized films on SiO$_2$ substrates were deposited at 0.2 Å s$^{-1}$ to a thickness of 50 nm. Top-contact devices were made by vapor depositing 50 nm thick gold electrodes onto the NDI-8CN$_2$ films.

The substrate/semiconductor interface optimization was performed on n$^+$ doped silicon wafers with 300 nm thermally grown SiO$_2$ where the SiO$_2$ surface was varied according to the following procedures. SiO$_2$ substrates were prepared by rinsing the wafer with acetone, methanol, and isopropanol, followed by oxygen plasma cleaning at 18 W for 5 minutes with a Harrick Plasma Cleaner/Sterilizer PDC-32G. HMDS substrates were prepared by exposing the cleaned SiO$_2$ substrates to HMDS vapor for 3 days until the aqueous contact angle was greater than about 90°. Polystyrene substrates were fabricated by spin-coating a 40 mg/mL solution of polystyrene in toluene onto a cleaned SiO$_2$ substrate at 2000 rpm for 45 seconds. The film was then placed in an 85° C. vacuum oven overnight.

Alternatively, flexible and transparent device substrates may also be fabricated as follows. Two different types of OFETs with transparent channels were prepared with NDI-8CN$_2$ semiconductor films. Flexible OFETs were fabricated on 3M CG 3720 overhead transparency films. The transparency films were first cleaned by sonication in detergent solution and deionized water, followed by plasma cleaning for 90 seconds. A thin film of aqueous PEDOT:PSS (1:1) solution from Baytron was then spin-cast onto the transparency at 2500 rpm for 1 minute and 20 seconds. The films were then annealed under vacuum at 80° C. for 24 hours. Next, a 600 nm thick transparent polymer dielectric (P-UV-013, Polyera Corporation, Illinois) was spin-coated onto the PEDOT:PSS film. The 50 nm NDI-8CN$_2$ film was then vapor-deposited (0.2 Å/s, $10^{-6}$ Torr) at a $T_d$ of 110° C. Gold S/D electrodes (20 nm) were vapor-deposited (0.2 Å/s, $10^{-7}$ Torr) through a shadow mask to give translucent S/D electrodes. Analogous rigid OFETs were fabricated on an ultrasmooth ITO/glass substrates with the same polymer dielectric as above. All other fabrication conditions were identical to those for the flexible transparent channel OFET.

The present teachings encompass embodiments in other specific forms without departing from the spirit or essential characteristics thereof. The foregoing embodiments are therefore to be considered in all respects illustrative rather than limiting on the present teachings described herein. Scope of the present invention is thus indicated by the appended claims rather than by the foregoing description, and all changes that come within the meaning and range of equivalency of the claims are intended to be embraced therein.

What is claimed is:

1. A compound of formula I or formula II:

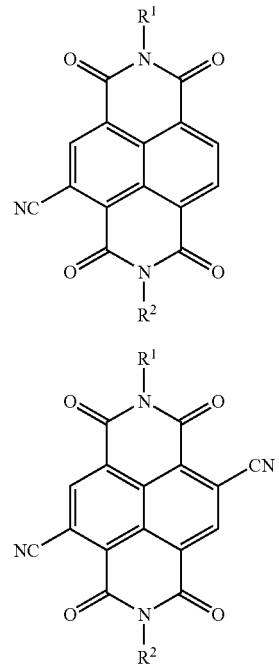

wherein:

$R^1$ and $R^2$ independently are selected from a) H, b) a $C_{1-20}$ alkyl group, c) a $C_{1-20}$ haloalkyl group, d) a $C_{2-20}$ alkenyl group, e) a $C_{2-20}$ alkynyl group, f) a $C_{3-10}$ cycloalkyl group, g) a $C_{6-14}$ aryl group, h) a 3-14 membered cycloheteroalkyl group, and i) a 5-14 membered heteroaryl group, wherein each of the $C_{1-20}$ alkyl group, the $C_{2-20}$ alkenyl group, the $C_{2-20}$ alkynyl group, the $C_{3-10}$ cycloalkyl group, the $C_{6-14}$ aryl group, the 3-14 membered cycloheteroalkyl group, and the 5-14 membered heteroaryl group is optionally substituted with 1-5 $R^a$ groups;

$R^a$, at each occurrence, is independently selected from a) a halogen, b) —CN, c) —NO$_2$, d) —N$^+$(R$^b$)$_3$, e) —S(O)$_m$R$^b$, f) —S(O)$_m$OR$^b$, g) —C(O)R$^b$, h) —C(O)OR$^b$, i) —(CH$_2$CH$_2$O)$_n$CH$_2$CH$_2$OH, and j) a $C_{1-20}$ haloalkyl group;

$R^b$, at each occurrence, is independently selected from a) H, b) a $C_{1-20}$ alkyl group, c) a $C_{1-20}$ haloalkyl group, d) a $C_{6-14}$ aryl group, e) a —(C$_{1-20}$ alkyl)—C$_{6-14}$ aryl group, and f) a —(C$_{1-20}$ haloalkyl)—C$_{6-14}$ aryl group;

m is 0, 1 or 2; and n is 1, 2, 3, 4, 5, 6, 7, 8, 9 or 10.

2. The compound of claim 1, wherein the compound is of formula I, and at least one of R$^1$ and R$^2$ is a $C_{1-20}$ alkyl group.

3. The compound of claim 2, wherein the compound is of formula I, and R$^1$ and R$^2$ are straight-chain $C_{3-16}$ alkyl groups.

4. The compound of claim 1, wherein the compound is of formula I, and at least one of R$^1$ and R$^2$ is a straight-chain $C_{1-20}$ fluoroalkyl group.

5. The compound of claim 1, wherein the compound is of formula I, and at least one of R$^1$ and R$^2$ is a $C_{3-10}$ cycloalkyl group.

6. The compound of claim 1 selected from N,N'-bis(n-octyl)-2-cyanonaphthalene-1,4,5,8-bis(dicarboximide) and N,N'-bis(n-octyl)-2,6-dicyanonaphthalene-1,4,5,8-bis(dicarboximide).

7. A thin film semiconductor comprising one or more compounds of claim 1.

8. A composite comprising a substrate and the thin film semiconductor of claim 7 deposited on the substrate.

9. A transistor device comprising the composite of claim 8.

10. A transparent organic transistor device comprising the composite of claim 8.

11. The compound of claim 1, wherein the compound is of formula I.

12. A thin film semiconductor comprising one or more compounds of claim 11.

13. A thin film semiconductor comprising one or more compounds of claim 2.

14. A thin film semiconductor comprising one or more compounds of claim 3.

15. A thin film semiconductor comprising one or more compounds of claim 4.

16. A thin film semiconductor comprising one or more compounds of claim 5.

17. A thin film semiconductor comprising a compound of claim 6, wherein the compound is N,N'-bis(n-octyl)-2-cyanonaphthalene-1,4,5,8-bis(dicarboximide).

18. A transistor device comprising the thin film semiconductor of claim 17.

19. A thin film semiconductor comprising a compound of claim 6, wherein the compound is N,N'-bis(n-octyl)-2,6-dicyanonaphthalene-1,4,5,8-bis(dicarboximide).

20. A transistor device comprising the thin film semiconductor of claim 19.

* * * * *